(12) United States Patent
Purschke et al.

(10) Patent No.: US 8,871,920 B2
(45) Date of Patent: Oct. 28, 2014

(54) LIPID BINDING NUCLEIC ACIDS

(75) Inventors: Werner Purschke, Berlin (DE); Sven Klussmann, Berlin (DE); Klaus Buchner, Berlin (DE); Frank Schwobel, Berlin (DE); Kai Hoehlig, Berlin (DE)

(73) Assignee: NOXXON Pharma AG, Berlin (DE)

( * ) Notice: Subject to any disclaimer, the term of this patent is extended or adjusted under 35 U.S.C. 154(b) by 184 days.

(21) Appl. No.: 13/642,555

(22) PCT Filed: Apr. 21, 2011

(86) PCT No.: PCT/EP2011/002068
§ 371 (c)(1),
(2), (4) Date: Feb. 8, 2013

(87) PCT Pub. No.: WO2011/131371
PCT Pub. Date: Oct. 27, 2011

(65) Prior Publication Data
US 2013/0165501 A1  Jun. 27, 2013

(30) Foreign Application Priority Data

Apr. 21, 2010 (EP) .................................... 10004253
Jan. 10, 2011 (EP) .................................... 11000117

(51) Int. Cl.
C07H 21/04 (2006.01)
G01N 33/92 (2006.01)
C12N 15/115 (2010.01)

(52) U.S. Cl.
CPC .......... *C12N 15/115* (2013.01); *C12N 2310/16* (2013.01); *G01N 33/92* (2013.01)
USPC ...................................................... 536/24.5

(58) Field of Classification Search
USPC ........................................................ 536/24.5
See application file for complete search history.

(56) References Cited

U.S. PATENT DOCUMENTS

| 6,225,063 B1 | 5/2001 | Khvorova |
| 7,862,812 B2 | 1/2011 | Sabbadini |
| 8,497,250 B2 | 7/2013 | Vater et al. |

OTHER PUBLICATIONS

Betat, "Aptamers . . . A," Biol Chem 384:1497-1500, 2003.
Vlassov, "Binding . . . complexes," PNAS 98:7706-7711, 2001.
Khvorova, "RNAs . . . membranes," PNAS 96:10649-10654, 1999.
Janas, "Specific . . . bilayers," NAR 34:2128-2136, 2006.
Janas & Janas, "The . . . targets," Cell Mol Lett 16:25-39, 2011.
Horii et al., "Development . . . aptamers," Molecules 15:5742-5755, 2010.
Visentin et al., "Validation . . . lineages," Cancer Cell 9:225-238, 2006.
Eulberg et al., "Spiegelmers: biostable aptamers," Chembiochem 4:979-983, 2003.
Vater et al., "Toward . . . prospects," Curr Opn Drug Disc Devel 6:253-261, 2003.
Rivera et al., "The . . . immunity," Nature Rev Imm 8:753-763, 2008.
Peters et al., "Sphingosine . . . system," Curr Opn Pharm 7:186-192, 2007.
Helmling et al., "Inhibition . . . spiegelmer," PNAS 101:13174-13179, 2004.
James, "Aptamers," in Encycl Anal Chem, Meyers, ed., Sec 2.4.2, 2000.
Leva et al., "GnRH . . . Antagonism," Chem Biol 9, 351-359, 2002.
Purschke et al. "A DNA . . . enterotoxin B," NAR 31, 3027-3032, 2003.
de Souza et al., "Novel . . . targets," Neuropsychpharm Rev, p. 1-17, 2008.

*Primary Examiner* — Brian Whiteman
(74) *Attorney, Agent, or Firm* — MDIP LLC

(57) ABSTRACT

The present invention is related to a nucleic acid molecule capable of binding to a lipid.

34 Claims, 11 Drawing Sheets

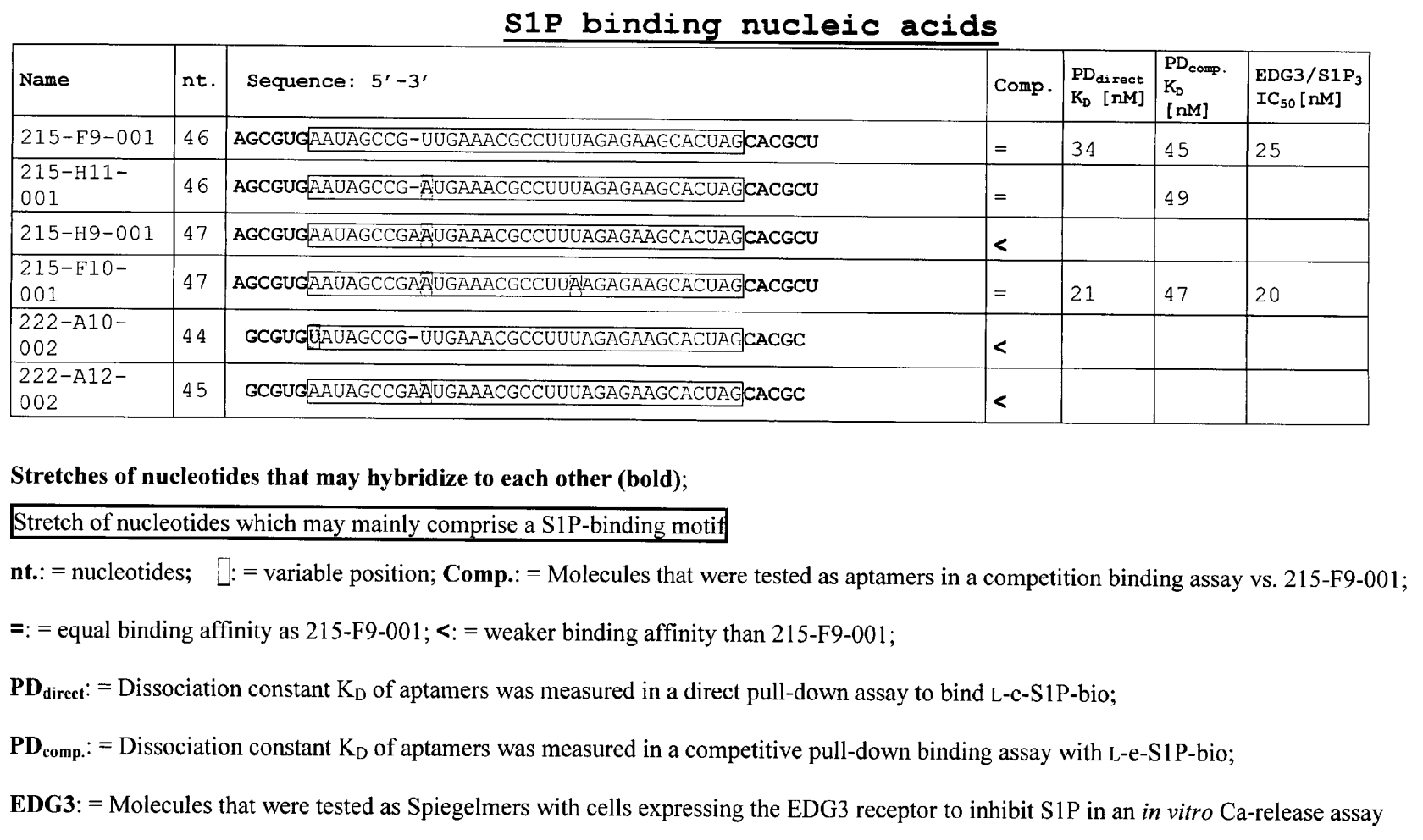

S1P binding nucleic acids

| Name | nt. | Sequence: 5'-3' | Comp. | PD$_{direct}$ K$_D$ [nM] | PD$_{comp.}$ K$_D$ [nM] | EDG3/S1P$_3$ IC$_{50}$ [nM] |
|---|---|---|---|---|---|---|
| 215-F9-001 | 46 | AGCGUGAAUAGCCG-UUGAAACGCCUUUAGAGAAGCACUAGCACGCU | = | 34 | 45 | 25 |
|

Derivatives of 215-F9-001

| Name | nt. | Sequence: 5'-3' | Comp. | PD$_{comp.}$ K$_D$ [nM] | EDG3/S1P$_3$ IC$_{50}$ [nM] |
|---|---|---|---|---|---|
| 215-F9-001 | 46 | AGCGUGAAUAGCCGUUGAAACGCCUUUAGAGAAGCACUAGCACGCU | = | 45 | 25 |
| 215-F9-002 | 44 | GCGUGAAUAGCCGUUGAAACGCCUUUAGAGAAGCACUAGCACGC | = | 53 | 31 |
| 215-F9-003 | 42 | CGUGAAUAGCCGUUGAAACGCCUUUAGAGAAGCACUAGCACG | = | 50 | |
| 215-F9-004 | 40 | GUGAAUAGCCGUUGAAACGCCUUUAGAGAAGCACUAGCAC | < | | |
| 215-F9-008 | 42 | GCUGAAUAGCCGUUGAAACGCCUUUAGAGAAGCACUAGCAGC | < | | |
| 215-F9-009 | 42 | GGUGAAUAGCCGUUGAAACGCCUUUAGAGAAGCACUAGCACC | < | | |

Stretches of nucleotides that may hybridize to each other (bold);

Stretch of nucleotides which may mainly comprise a S1P-binding motif nt.: = nucleotides;

Comp.: = Molecules that were tested as aptamers in a competition binding assay vs. 215-F9-001;

=: = equal binding affinity as 215-F9-001; <: = weaker binding affinity than 215-F9-001;

PD$_{comp.}$: = Dissociation constant K$_D$ of aptamers was measured in a competitive pull-down binding assay with L-e-S1P-bio;

EDG3: = Molecules that were tested as Spiegelmers with cells expressing the EDG3 receptor to inhibit S1P in an *in vitro* Ca-release assay

Fig. 2

F9001PEG = Spiegelmer 215-F9-001-5'-PEG = NOX-S92
F9002PEG = Spiegelmer 215-F9-002-5'PEG = NOX-S-91

| | |
|---|---|
| dose: | iv., 20 mg/kg BW |
| adm. volume: | 10 ml/kg BW |
| data: | mean±SEM, n=5 |
| statistics: | Dunnett's Multiple Comparison Test, **p<0.01 (compared to predose) |
| specie: | C57BL-6, female |
| BW: | 20-28 g |

| name | sequence: 5'-3' | pull-down ranking | competitive pull-down assay ($K_D$) |
|---|---|---|---|
| L-S1P-215-F9-002 | GCGUGAAUAGCCGUUGAAACGCCUUUAGAGAAGCACUAGCACGC | | 31.5±3.1 nM |
| L-S1P-215-F9-002-D01 | dGCGUGAAUAGCCGUUGAAACGCCUUUAGAGAAGCACUAGCACGC | + (F9-002) | |
| L-S1P-215-F9-002-D11 | GCGUGAAUAGdCCGUUGAAACGCCUUUAGAGAAGCACUAGCACGC | + (F9-002) | |
| L-S1P-215-F9-002-D19 | GCGUGAAUAGCCGUUGAAdACGCCUUUAGAGAAGCACUAGCACGC | + (F9-002) | 16nM |
| L-S1P-215-F9-002-D21 | GCGUGAAUAGCCGUUGAAACdGCCUUUAGAGAAGCACUAGCACGC | + (F9-002) | 11.3±2.1 nM |
| L-S1P-215-F9-002-D22 | GCGUGAAUAGCCGUUGAAACGdCCUUUAGAGAAGCACUAGCACGC | + (F9-002) | 30nM |
| L-S1P-215-F9-002-D32 | GCGUGAAUAGCCGUUGAAACGCCUUUAGAGAdAGCACUAGCACGC | + (F9-002) | |
| | | | |
| L-S1P-215-F9-002-D21-22 | GCGUGAAUAGCCGUUGAAACdGdCCUUUAGAGAAGCACUAGCACGC | = (D21) | |
| L-S1P-215-F9-002-D21-19 | GCGUGAAUAGCCGUUGAAdACdGCCUUUAGAGAAGCACUAGCACGC | + (D21) | 6nM |
| L-S1P-215-F9-002-D21-19-22 | GCGUGAAUAGCCGUUGAAdAdC dG dCCUUUAGAGAAGCACUAGCACGC | = (D21-D19) | |
| L-S1P-215-F9-002-D01-19-21-32 | dGCGUGAAUAGCCGUUGAAdACdGCCUUUAGAGAdAGCACUAGCACGC | + (D21-D19) | 5nM |
| L-S1P-215-F9-002-D01-11-19-21-32 | dGCGUGAAUAGdCCGUUGAAdACdGCCUUUAGAGAdAGCACUAGCACGC | + (D21-D19) | 5nM |

= equal binding as spiegelmer L-S1P-215-F9-002-D21 (= D21) or spiegelmer L-S1P-215-F9-002-D21-19 (= D21-D19), determined by competitive pull-down ranking assay + improved binding in comparison to spiegelmer L-S1P-215-F9-002 (= F9-002), L-S1P-215-F9-002-D21 (= D21) or spiegelmer L-S1P-215-F9-002-D21-19 (= D21-D19), determined by competitive pull-down ranking assay

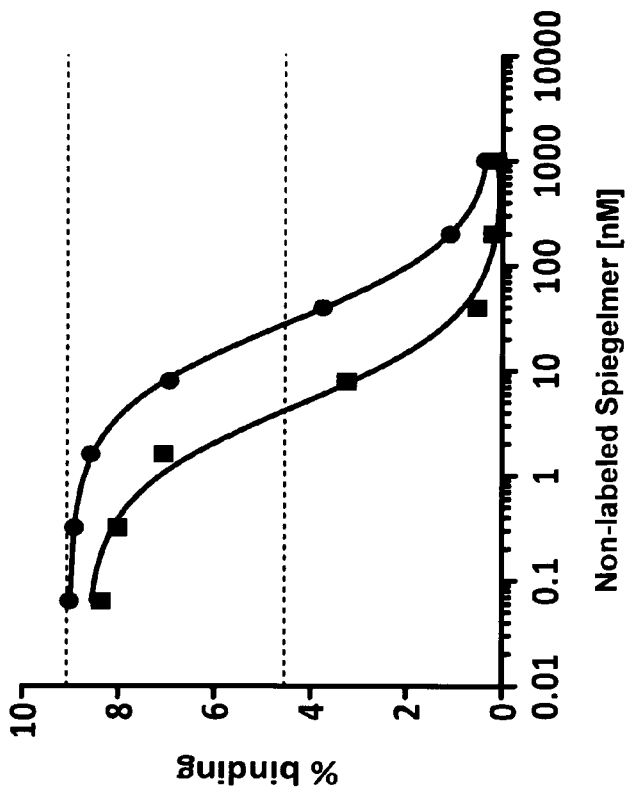
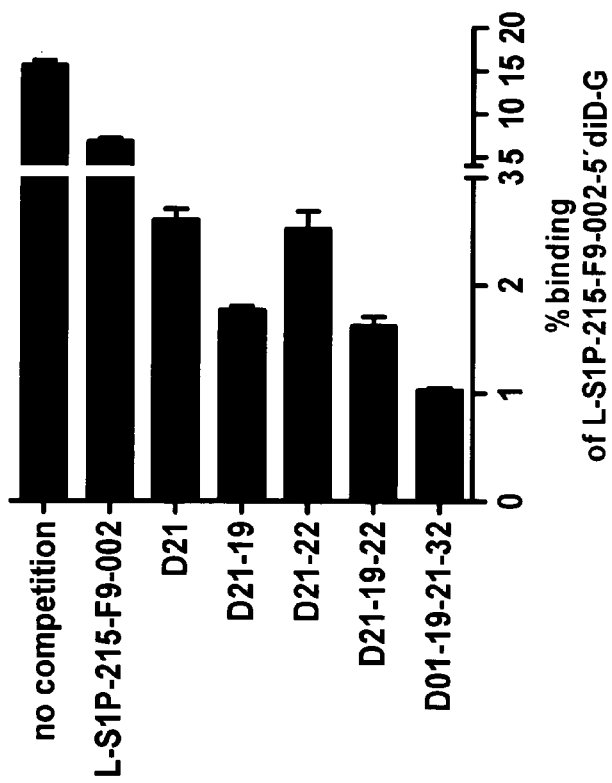
D21 = L-S1P-215-F9-002-D21
D21-19 = L-S1P-215-F9-002-D21-19
D21-22 = L-S1P-215-F9-002-D21-22
D21-19-22 = L-S1P-215-F9-002-D19-21-22
D01-19-21-32 = L-S1P-215-F9-002-D01-19-21-32
Fig. 8

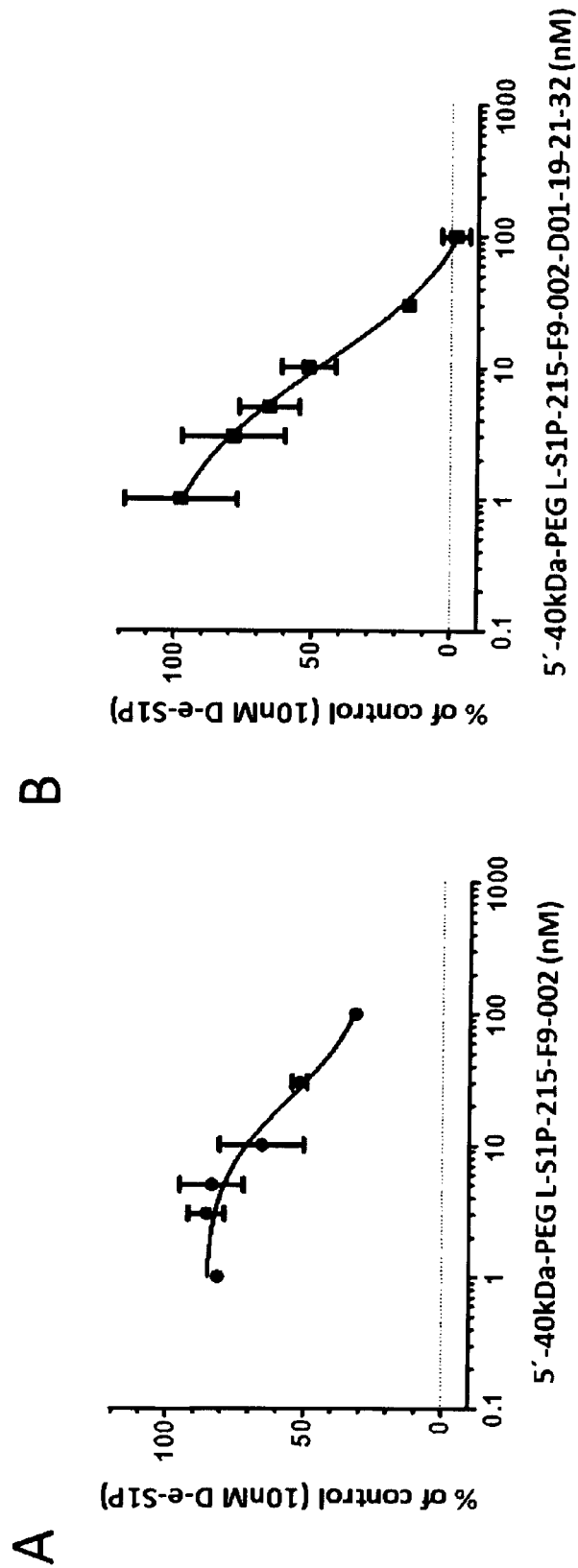
Fig. 9 (A and B)

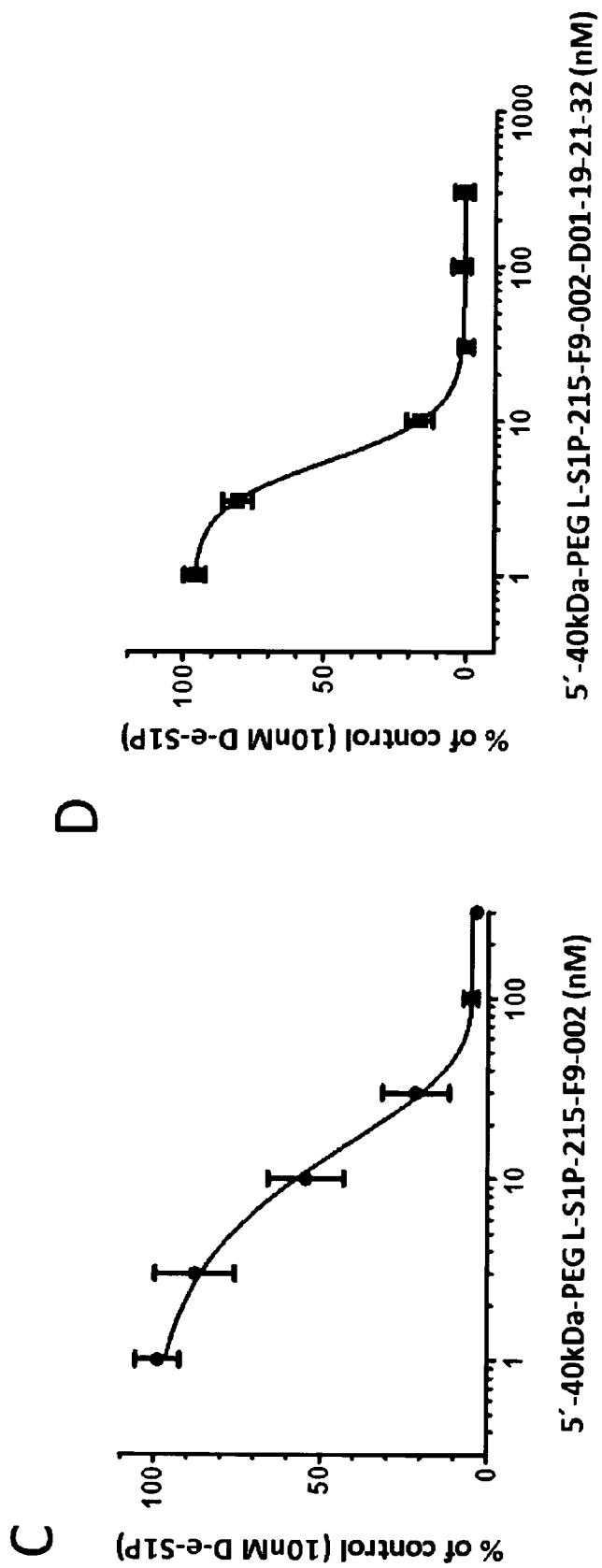
Fig. 9 (C and D)

| Compound | Stimulation | IC$_{50}$ values [M] |
|---|---|---|
| NOX-S91 | [S1P] (100 nM) | $7.5 \times 10^{-7}$ M |
| NOX-S93 | [S1P] (100 nM) | $3.4 \times 10^{-7}$ M |
| NOX-S91 | [VEGF-A] (25 ng/ml) | $2.1 \times 10^{-7}$ M |
| NOX-S93 | [VEGF-A] (25 ng/ml) | $2.4 \times 10^{-7}$ M |
| Sunitinib | [VEGF-A] (25 ng/ml) | $2.5 \times 10^{-7}$ M |

Fig. 10

LIPID BINDING NUCLEIC ACIDS

The present invention is related to a nucleic acid molecule capable of a binding to a lipid, preferably a phospholipid, more preferably sphingosine 1-phosphate, the use thereof for the manufacture of a medicament, a diagnostic agent, and a detecting agent, respectively, a composition comprising such nucleic acid molecule, a complex comprising such nucleic acid molecule, a method for screening of an antagonist of an activity mediated by the lipid or an analogue of a lipid using such nucleic nucleic acid molecule, and a method for the detection of such nucleic acid molecule.

Lipids and lipid derivatives are best known for their function as structural elements in cellular membranes or as a substrate for β-oxidation or glycolysis. More recently, lipids and lipid derivatives have become recognized as signaling molecules that play an important role in disease. There are many examples of bioactive lipid signaling molecules including phospholipids such as phosphatidyl inositol (abbr. PI), phosphatidyl serine (abbr. PS), diacylglyceride (abbr. DAG), phosphatidyl glycerol (abbr. PG) and phosphatidic acid (abbr. PA), lysophosphatidyl choline, platelet activating factor and cardiolipins. Other examples of lipid signaling molecules include eicosanoids, which encompass cannabinoids, prostaglandins, isoeicosanoids and leukotrienes. Lipids can act as second messengers or through the direct interaction with their own specific receptor. Lipid signaling pathways are activated through various different stimuli and are involved in the regulation of a diverse array of cellular processes including adhesion, motility, proliferation, apoptosis and differentiation. Sphingolipids and their derivatives have extracellular and intracellular signaling function and play important roles in human disease. An additional and important class of lipid signaling molecules are sphingolipids; they include ceramide, ceramide-1-phosphate, sphingomyelin, sphingosine, sphingosine-1-phosphate, sphinganine, and sphinganine-1-phosphate.

Sphingosine 1-phosphate (abbr. S1P) is a 380 Dalton phospholipid with the molecular formula $C_{18}H_{38}NO_5P$. Once considered simply a breakdown product of ceramide, S1P is now known to have an important function in diverse biological processes such as cell growth, cell proliferation, angiogenesis, and lymphocyte trafficking (for review see Kim et al., Biochim Biophys Acta. 2009 1791:692-6; Maceyka et al, J Lipid Res. 2009 50 Suppl:S272-6; Takabe et al., Pharmacol Rev. 2008 60(2):181-95).

Among its other functions S1P has antiapoptotic effects and promotes cell growth and proliferation. Its precursors sphingosine and ceramide have opposite functions, inducing cell cycle arrest and cell death. Because S1P and its precursors exhibit such opposing actions it is thought that the relative balance of the different sphingosine metabolites rather than their absolute amount—controlled primarily by the interplay of sphingosine phosphatases and sphingosine kinases—determines cell fate. This complex regulatory system is referred to as the "sphingolipid rheostat".

Recent work has implicated S1P and its metabolites, as well as its precursor ceramide, as second messengers for TNF-α, IL1β, and other cytokines. Various lines of evidence support S1P's role as a second messenger responsible for cell proliferation and survival. At the same time many of S1P's biological effects, however, are the result of acting as a ligand for the five G-protein coupled receptors for S1P (abbr. S1PR) on the cell surface. Originally identified as orphan receptors and named the endothelial differentiation gene (abbr. EDG), they have now been renamed EDG1/S1P$_1$, EDG5/S1P$_2$, EDG3/S1P$_3$, EDG6/S1P$_4$, EDG8/S1P$_5$, and characterized. Each receptor couples to heterodimeric G-proteins (Gq, G1, G12-13), activating downstream signaling molecules such as small GTPases of the Rho family (Zhou and Murthy, Am J Physiol Cell Physiol. 2004, 286:C1130-C1138; Kume et al, J Pharmacol Exp Ther. 2007 320:766-773), mitogen-activated protein kinase (Guo et al., Eur J. Biochem. 1998 257:403-408; Sato et al., Mol. Pharmacol. 1999 55:126-133; Dikic et al., Nature. 1996 383:547-550.), phospholipase C/D (Okamoto et al, J Biol. Chem. 1998 273:27104-27110; Gonda et al., Biochem J. 1999 337:67-75; Banno et al., J Biol. Chem. 1999 274:27385-27391) and others. The expression of the S1PR is widespread and S1P influences a vast range of cellular responses including adhesion, contraction, motility, morphogenesis, proliferation and differentiation, implicating S1P in the regulation of vascular tone, wound healing, trafficking of immune cells, neuronal signaling, angiogenesis, reproduction and cardiovascular function. The spectrum of responses depends on the pattern of receptor expression in the cells and tissues and the corresponding effector. Thus, activation of a particular S1PR can have the opposite effect than activation of another in, for example, endothelial cell (Lee et al., Mol. Cell. 2001 8:693-704.; Kimura et al., Biochem J. 2000 348:71-76.; Ryu et al., Circ Res. 2002 90:325-332.). Activation of one S1PR can differentially regulate GTPases of the Rho family (Garcia et al., J Clin Invest. 2001 108:689-701; Gon et al., Proc Natl Acad Sci USA. 2005 102:9270-9275; Liu et al., J Clin Invest. 2000 106:951-961). In addition, there is crosstalk to other growth factor signaling pathways.

S1P present in circulating blood and lymph is made primarily by platelets, activated mast cells and mononuclear phagocytes, and secreted. S1P is found at concentrations between 0.1 to 1 mM, sometimes up to 5 mM, but only a fraction is available to activate S1PRs as most S1P is bound to albumin or other plasma proteins. The alteration of the endogenous levels of S1P can lead to pathophysiological conditions, including inflammation and autoimmune diseases, asthma, angiogenesis, heart disease, cancer, ocular disease, and cerebrovascular disease.

Because many of the effects of S1P are thought to be mediated by the interaction or binding of S1P with one or several S1PRs, therapeutic approaches have concentrated on targeting the receptors. Numerous different S1P receptor antagonists and agonists have been identified and described. They differ in specificity and affinity for the various S1PRs and thus display various functional profiles. The most advanced compound, Fingolimod, also know as FTY720, is a prodrug and is phosphorylated in vivo. The phosphohorylated form is an agonist for the S1PRs S1P$_1$, S1P$_3$, S1P$_4$ and S1P$_5$ and was shown to be highly efficacious in models of transplantation and autoimmune disease. It is currently in phase 3 clinical trials for the treatment of multiple sclerosis. Because of the opposing effects of the different S1PR, there is interest in identifying molecules with specific selectivities for the various receptors. Another approach to interfere with S1P dependent pathophysiology is to affect the endogenous S1P levels. This could be achieved by targeting S1P kinases to alter the amount of S1P made through phorsphorylation of sphingosine or by targeting S1P phosphatases to affect the amount of S1P that is being dephosphorylated. Another approach to affect the endogenous levels of bioactive S1P is through the direct inhibition of S1P effects by a molecular interaction with a neutralizing agent. The present invention describes a way to neutralize S1P.

The problem underlying the present invention is to provide a means which specifically interacts with a lipid, preferably a phospholipid, more preferably S1P. More specifically, the problem underlying the present invention is to provide for a nucleic acid based means which specifically interacts with and/or to a lipid, preferably a phospholipid, more preferably S1P.

A further problem underlying the present invention is to provide a means for the manufacture of a medicament for the treatment of a human or non-human disease, whereby the disease is characterized by a lipid, preferably a phospholipid, more preferably S1P, being either directly or indirectly involved in the pathogenetic mechanism of such disease.

A still further problem underlying the present invention is to provide a means for the manufacture of a diagnostic agent for the diagnosing of a disease, whereby the disease is characterized by a lipid, preferably a phospholipid, more preferably S1P being, either directly or indirectly involved in the pathogenetic mechanism of such disease.

These and other problems underlying the present invention are solved by the subject matter of the attached independent claims. Preferred embodiments may be taken from the dependent claims.

More specifically, the problem underlying the present invention is solved in a first aspect which is also the first embodiment of the first aspect, by a nucleic acid molecule capable of binding to a lipid.

In a second embodiment of the first aspect which is also an embodiment of the first embodiment of the first aspect, the nucleic acid is an antagonist of an activity mediated by the lipid.

In a third embodiment of the first aspect which is also an embodiment of the first and the second embodiment of the first aspect, the lipid is a phospholipid, preferably the phospholipid is sphingosine 1-phosphate.

In a fourth embodiment of the first aspect which is also an embodiment of the first, the second and the third embodiment of the first aspect, the nucleic acid molecule comprises a central stretch of nucleotides, wherein the central stretch of nucleotides comprises a nucleotide sequence of

```
5' WAUUGCCGAWUGUAACGCCUUWAGAGAAAGCACUAG 3'
or
5' WAUUGCCGWUGUAACGCCUUWAGAGAAAGCACUAG 3'
``` and wherein the lipid is preferably sphingosine 1-phosphate.

In a fifth embodiment of the first aspect which is also an embodiment of the fourth embodiment of the first aspect, the central stretch of nucleotides comprises a nucleotide sequence selected from the group of 5' AAUAGCCG-UUGAAACGCCUUUAGAGAAGCACUAG 3', 5' AAUAGCCGAUGAAACGCCUUUAGAGAAGCACUAG 3' and 5' AAUAGCCGAAUGAAACGCCUUAA-GAGAAGCACUAG 3'.

In a sixth embodiment of the first aspect which is also an embodiment of the fourth and the fifth embodiment of the first aspect, the nucleic acid molecule comprises in 5'→3' direction a first terminal stretch of nucleotides, the central stretch of nucleotides and a second terminal stretch of nucleotides, wherein the first terminal stretch of nucleotides comprises three to six nucleotides, and the second terminal stretch of nucleotides comprises three to six nucleotides.

In a seventh embodiment of the first aspect which is also an embodiment of the fourth and the fifth embodiment of the first aspect, the nucleic acid molecule comprises in 5'→3' direction a second terminal stretch of nucleotides, the central stretch of nucleotides and a first terminal stretch of nucleotides, wherein the first terminal stretch of nucleotides comprises three to six nucleotides, and the second terminal stretch of nucleotides comprises three to six nucleotides.

In an eighth embodiment of the first aspect which is also an embodiment of the sixth and the seventh embodiment of the first aspect, the first terminal stretch of nucleotides comprises a nucleotide sequence of 5' $X_1X_2X_3$SUG 3' and the second terminal stretch of nucleotides comprises a nucleotide sequence of 5' CAS$X_4X_5X_6$ 3', wherein $X_1$ is A or absent, $X_2$ is G or absent, $X_3$ is S or absent, $X_4$ is S or absent, $X_5$ is C or absent, and $X_6$ is U or absent.

In a ninth embodiment of the first aspect which is also an embodiment of the sixth, the seventh and the eighth embodiment of the first aspect, the first terminal stretch of nucleotides comprises a nucleotide sequence of 5' $X_1X_2X_3$SUG 3' and the second terminal stretch of nucleotides comprises a nucleotide sequence of 5' CAS$X_4X_5X_6$ 3', wherein a) $X_1$ is A, $X_2$ is G, $X_3$ is S, $X_4$ is S, $X_5$ is C, and $X_6$ is U or b) $X_1$ is absent, $X_2$ is G, $X_3$ is S, $X_4$ is S, $X_5$ is C, and $X_6$ is U or c) $X_1$ is A, $X_2$ is G, $X_3$ is S, $X_4$ is S, $X_5$ is C, and $X_6$ is absent or d) $X_1$ is absent, $X_2$ is G, $X_3$ is S, $X_4$ is S, $X_5$ is C, and $X_6$ is absent.

In a tenth embodiment of the first aspect which is also an embodiment of the sixth, the seventh, the eighth and the ninth embodiment of the first aspect, a) the first terminal stretch of nucleotides comprises a nucleotide sequence of 5' AGCGUG 3' and the second terminal stretch of nucleotides comprises a nucleotide sequence of 5' CACGCU 3' or b) the first terminal stretch of nucleotides comprises a nucleotide sequence of 5' GCGUG 3' and the second terminal stretch of nucleotides comprises a nucleotide sequence of 5' CACGC 3'.

In an eleventh embodiment of the first aspect which is also an embodiment of the sixth, the seventh and the eighth embodiment of the first aspect, the first terminal stretch of nucleotides comprises a nucleotide sequence of 5' $X_1X_2X_3$SUG 3' and the second terminal stretch of nucleotides comprises a nucleotide sequence of 5' CAS$X_4X_5X_6$ 3', wherein a) $X_1$ is absent, $X_2$ is absent, $X_3$ is S, $X_4$ is S, $X_5$ is C, and $X_6$ is absent or b) $X_1$ is absent, $X_2$ is G, $X_3$ is S, $X_4$ is S, $X_5$ is absent, and $X_6$ is absent or c) $X_1$ is absent, $X_2$ is absent, $X_3$ is S, $X_4$ is S, $X_5$ is absent, and $X_6$ is absent.

In a twelfth embodiment of the first aspect which is also an embodiment the sixth, the seventh, the eighth and the eleventh embodiment of the first aspect, a) the first terminal stretch of nucleotides comprises a nucleotide sequence of 5' CGUG 3' and the second terminal stretch of nucleotides comprises a nucleotide sequence of 5' CACG 3' or b) the first terminal stretch of nucleotides comprises a nucleotide sequence of 5' GCUG 3' and the second terminal stretch of nucleotides comprises a nucleotide sequence of 5' CAGC 3' or c) the first terminal stretch of nucleotides comprises a nucleotide sequence of 5' GGUG 3' and the second terminal stretch of nucleotides comprises a nucleotide sequence of 5' CACC 3', preferably the first terminal stretch of nucleotides comprises a nucleotide sequence of 5' CGUG 3' and the second terminal stretch of nucleotides comprises a nucleotide sequence of 5' CACG 3'.

In a thirteenth embodiment of the first aspect which is also an embodiment of the sixth, the seventh and the eighth embodiment of the first aspect, the first terminal stretch of nucleotides comprises a nucleotide sequence of 5' $X_1X_2X_3$SUG 3' and the second terminal stretch of nucleotides comprises a nucleotide sequence of 5' CAS$X_4X_5X_6$ 3', wherein $X_1$ is absent, $X_2$ is absent, $X_3$ is S or absent, $X_4$ is S or absent, $X_5$ is absent, and $X_6$ is absent.

In a fourteenth embodiment of the first aspect which is also an embodiment of the sixth, the seventh, the eighth and the thirteenth embodiment of the first aspect, the first terminal stretch of nucleotides comprises a nucleotide sequence of 5' GUG 3' and the second terminal stretch of nucleotides comprises a nucleotide sequence of 5' CAC 3'.

In a fifteenth embodiment of the first aspect which is also an embodiment of the fourth, the fifth, the sixth, the seventh, the eighth, the ninth, the tenth, the eleventh, the twelfth, the thirteenth and the fourteenth embodiment of the first aspect, the central stretch of nucleotides is essential for binding to sphingosine 1-phosphate.

In a sixteenth embodiment of the first aspect which is also an embodiment of the sixth, the seventh, the eighth, the ninth, the tenth, the eleventh, the twelfth, the thirteenth, the fourteenth and the fifteenth embodiment of the first aspect, the first terminal stretch of nucleotides and the second terminal stretch of nucleotides optionally hybridize with each other, wherein upon hybridization a double-stranded structure is formed.

In a seventeenth embodiment of the first aspect which is also an embodiment of the sixteenth embodiment of the first aspect, the double-stranded structure consists of three to six basepairs.

In an eighteenth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth and the seventeenth embodiment of the first aspect, the nucleic acid molecule comprises a nucleotide sequence according to any one of SEQ. ID. Nos 12 to 26, 41 and 42, preferably a nucleotide sequence according to any one of SEQ.ID.Nos 12, 13, 15, 18, 19, 23 to 26, 41 and 42, more preferably a nucleotide sequence according to any one of SEQ ID Nos 12, 18, 23, 24, 41 and 42.

In a nineteenth embodiment of the first aspect which is also an embodiment of the first, the second and the third embodiment of the first aspect, the nucleic acid molecule comprises a nucleotide sequence according to SEQ. ID. NO. 18 or a nucleic acid molecule which is homologous thereto, wherein the homology is at least 85%.

In a twentieth embodiment of the first aspect which is also an embodiment of the first, the second and the third embodiment of the first aspect, the nucleic acid molecule comprises a nucleotide sequence according to SEQ. ID. NO.41 or a nucleic acid molecule which is homologous thereto, wherein the homology is at least 85%.

In a twenty-first embodiment of the first aspect which is also an embodiment of the first, the second and the third embodiment of the first aspect, the nucleic acid molecule comprises a nucleotide sequence according to SEQ. ID. NO. 42 or a nucleic acid molecule which is homologous thereto, wherein the homology is at least 85%.

In a twenty-second embodiment of the first aspect which is also an embodiment of the first, the second and the third embodiment of the first aspect, the affinity of the nucleic acid molecule is increased compared to a reference nucleic acid molecule, wherein the reference nucleic acid molecule comprises a nucleotide sequence according to SEQ. ID. NO. 18 and wherein the reference nucleic acid molecule consists of ribonucleotides, wherein the nucleic acid molecule comprises a nucleotide sequence according to SEQ. ID. NO. 18 and wherein one or more nucleotides of the nucleotide sequence according to SEQ. ID. No. 18 is a deoxyribonucleotide rather than a ribonucleotide.

In a twenty-third embodiment of the first aspect which is also an embodiment of the twenty-second embodiment of the first aspect, the nucleic acid molecule comprises a nucleotide sequence according to any one of SEQ.ID.Nos 27 to 37, 39 and 40, preferably a nucleotide sequence according to any one of SEQ.ID.Nos 30, 34 to 37, 39 and 40, more preferably a nucleotide sequence according to any one of SEQ. ID. Nos. 36, 37, 39 and 40.

In a twenty-fourth embodiment of the first aspect which is also an embodiment of the twenty-third embodiment of the first aspect, the nucleic acid molecule comprises a nucleotide sequence according to SEQ. ID. NO. 36 or a nucleic acid molecule which is homologous thereto, wherein the homology is at least 85%, wherein the homologous nucleic acid comprises ribonucleotides and at least one deoxyribonucleotide.

In a twenty-fifth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, the nucleic acid molecule comprises a modification group, wherein excretion rate from an organism of the nucleic acid molecule comprising the modification group is decreased compared to a nucleic acid not comprising the modification group.

In a twenty-sixth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, the nucleic acid molecule comprises a modification group, wherein the nucleic acid molecule comprising the modification group has an increased retention time in an organism compared to a nucleic acid molecule not comprising the modification group.

In a twenty-seventh embodiment of the first aspect which is also an embodiment of the twenty-fifth and the twenty-sixth embodiment of the first aspect, the modification group is selected from the group comprising biodegradable and non-biodegradable modifications, preferably the modification group is selected from the group comprising of polyethylene glycol, linear polyethylene glycol, branched polyethylene glycol, hydroxyethyl starch, a peptide, a protein, a polysaccharide, a sterol, polyoxypropylene, polyoxyamidate and poly(2-hydroxyethyl)-L-glutamine.

In a twenty-eighth embodiment of the first aspect which is also an embodiment of twenty-seventh embodiment of the first aspect, the modification group is a polyethylene glycol, preferably consisting of a linear polyethylene glycol or branched polyethylene glycol wherein the molecular weight of the polyethylene glycol is preferably from about 20,000 to about 120,000 Da, more preferably from about 30,000 to about 80,000 Da and most preferably about 40,000 Da.

In a twenty-ninth embodiment of the first aspect which is also an embodiment of the twenty-seventh and the twenty-eighth embodiment of the first aspect, wherein the modification group is hydroxyethyl starch, wherein preferably the molecular weight of the hydroxyethyl starch is from about 50 to about 1000 kDa, more preferably from about 100 to about 700 kDa and most preferably from 200 to 500 kDa.

In a thirtieth embodiment of the first aspect which is also an embodiment of the twenty-fifth, the twenty-sixth, the twenty-seventh, the twenty-eighth and the twenty-ninth embodiment of the first aspect, the modification group is coupled to the nucleic acid molecule via a linker, whereby preferably the linker is a biodegradable linker.

In a thirty-first embodiment of the first aspect which is also an embodiment of the twenty-fifth, the twenty-sixth, the twenty-seventh, the twenty-eighth, the twenty-ninth and the thirtieth embodiment of the first aspect, the modification group is coupled to the 5'-terminal nucleotide and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule.

In a thirty-second embodiment of the first aspect which is also an embodiment of the twenty-fifth, the twenty-sixth, the twenty-seventh, the twenty-eighth, the twenty-ninth, the thirtieth and the thirty-first embodiment of the first aspect, the organism is an animal or a human body, preferably a human body.

In a thirty-third embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first and the thirty-second embodiment of the first aspect, the nucleotides of or the nucleotides forming the nucleic acid molecule are L-nucleotides.

In a thirty-fourth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second and the thirty-third embodiment of the first aspect, the nucleic acid molecule is an L-nucleic acid.

In a thirty-fifth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third and the thirty-fourth embodiment of the first aspect, the nucleic acid molecule comprises at least one binding moiety which is capable of binding sphingosine 1-phosphate, wherein such binding moiety consists of L-nucleotides.

In a thirty-sixth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth and thirty-fifth embodiment of the first aspect, the nucleic acid molecule is for use in a method for the treatment and/or prevention of a disease.

In a thirty-seventh embodiment of the first aspect which is also an embodiment of the thirty-sixth embodiment of the first aspect, the disease is treated or ameliorated by inhibition of angiogenesis and/or fibrosis.

In a thirty-eighth embodiment of the first aspect which is also an embodiment of the thirty-sixth and the thirty-seventh embodiment of the first aspect, the disease is an ocular diseases, preferably such ocular disease is selected from the group comprising age-related macular degeneration, diabetic retinopathy with diabetic macular edema, retinal pigmented epithelium detachment in either age-related macular degeneration or diabetic retinopathy, proliferative vitreoretinopathy and retinal fibrosis in age-related macular degeneration or diabetic retinopathy.

In a thirty-ninth embodiment of the first aspect which is also an embodiment of the thirty-sixth embodiment of the first aspect, the disease is treated or ameliorated by inhibition of angiogenesis and/or proliferation.

In a fortieth embodiment of the first aspect which is also an embodiment of the thirty-sixth, the thirty-seventh, the thirty-eighth and the thirty-ninth embodiment of the first aspect, the disease is cancer, preferably such cancer is selected from the group comprising breast cancer, ovarian cancer, melanoma, lung cancer, hyperplasia such as prostate hyperplasia.

In a forty-first embodiment of the first aspect which is also an embodiment of the thirty-sixth embodiment of the first aspect, the disease is an inflammatory disease, wherein such inflammatory disease is selected from the group comprising autoimmune disease, pneumonia, sepsis and trauma such as ventilator-induced lung injury.

In a forty-second embodiment of the first aspect which is also an embodiment of the forty-first embodiment of the first aspect, the autoimmune disease is selected from the group comprising multiple sclerosis, rheumatoid arthritis, psoriasis, asthma and inflammatory bowel disease.

The problem underlying the present invention is solved in a second aspect which is also the first embodiment of the second aspect, by a pharmaceutical composition comprising a nucleic acid molecule as defined in any one of the embodiments of the first aspect and optionally a further constituent, wherein the further constituent is selected from the group comprising pharmaceutically acceptable excipients, pharmaceutically acceptable carriers and pharmaceutically active agents.

In a second embodiment of the second aspect which is also an embodiment of the first embodiment of the second aspect, the pharmaceutical composition comprises a nucleic acid molecule as defined in any one of the embodiments of the first aspect and a pharmaceutically acceptable carrier.

The problem underlying the present invention is solved in a third aspect which is also the first embodiment of the third aspect, by the use of a nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect for the manufacture of a medicament.

In a second embodiment of the third aspect which is also an embodiment of the first embodiment of the third aspect, the medicament is for use in human medicine or for use in veterinary medicine.

The problem underlying the present invention is solved in a fourth aspect which is also the first embodiment of the fourth aspect, by the use of a nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect for the manufacture of a diagnostic means.

In a third embodiment of the third aspect which is also an embodiment of the first embodiment of the third aspect, the medicament is for the treatment and/or prevention of ocular diseases, cancer, or inflammatory disease.

In a fourth embodiment of the third aspect which is also an embodiment of the third embodiment of the third aspect, the ocular disease is selected from the group comprising age-related macular degeneration, diabetic retinopathy with diabetic macular edema, retinal pigmented epithelium detachment in either age-related macular degeneration or diabetic retinopathy, proliferative vitreoretinopathy and retinal fibrosis in age-related macular degeneration or diabetic retinopathy.

In a fifth embodiment of the third aspect which is also an embodiment of the third embodiment of the third aspect, the cancer is selected from the group comprising breast cancer, ovarian cancer, melanoma, lung cancer, hyperplasia such prostate hyperplasia.

In a sixth embodiment of the third aspect which is also an embodiment of the third embodiment of the third aspect, the inflammatory disease is selected from the group comprising autoimmune disease, pneumonia, sepsis and trauma such as ventilator-induced lung injury.

In a seventh embodiment of the third aspect which is also an embodiment of the sixth embodiment of the third aspect, the autoimmune disease is selected from the group comprising multiple sclerosis, rheumatoid arthritis, psoriasis, asthma and inflammatory bowel disease.

The problem underlying the present invention is solved in a fifth aspect which is also the first embodiment of the fifth aspect, by a complex comprising a nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect and a lipid, wherein preferably the complex is a crystalline complex.

In a second embodiment of the fifth aspect which is also an embodiment of the first embodiment of the fifth aspect, the lipid is a phospholipid, preferably the phospholipid is sphingosine 1-phosphate.

The problem underlying the present invention is solved in a sixth aspect which is also the first embodiment of the sixth aspect, by the use of a nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect for the detection of a lipid.

In a second embodiment of the sixth aspect which is also an embodiment of the first embodiment of the sixth aspect, the lipid is a phospholipid, preferably the phospholipid is sphingosine 1-phosphate.

The problem underlying the present invention is solved in a seventh aspect which is also the first embodiment of the seventh aspect, by a method for the screening of an antagonist of an activity mediated by a lipid or an analogue of the lipid comprising the following steps:
  providing a candidate antagonist of the of the activity mediated by the lipid and/or an analogue of the lipid,
  providing a nucleic acid as defined in any one of the embodiments of the first aspect,
  providing a test system which provides a signal in the presence of an antagonist of the activity mediated by the lipid and/or an analogue of the lipid, and
  1.—determining whether the candidate antagonist of the activity mediated by the lipid is an antagonist of the lipid and/or an analogue of the lipid.

In a second embodiment of the seventh aspect which is also an embodiment of the first embodiment of the seventh aspect, the lipid is a phospholipid, preferably the phospholipid is sphingosine 1-phosphate.

The problem underlying the present invention is solved in an eighth aspect which is also the first embodiment of the eighth aspect, by a kit for the detection of a lipid comprising a nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect, wherein preferably the lipid is a phospholipid, wherein more preferably the phospholipid is sphingosine 1-phosphate.

The problem underlying the present invention is solved in a ninth aspect which is also the first embodiment of the ninth aspect, by a method for the detection of a nucleic acid as defined in any one of the embodiments of the first aspect in a sample, wherein the method comprises the steps of:
  a) providing a capture probe, wherein the capture probe is at least partially complementary to a first part of the nucleic acid molecule as defined in any one of the embodiments of the first aspect, and a detection probe, wherein the detection probe is at least partially complementary to a second part of the nucleic acid molecule as defined in any one of the embodiments of the first aspect, or, alternatively, the capture probe is at least partially complementary to a second part of the nucleic acid molecule as defined in any one of the embodiments of the first aspect and the detection probe is at least partially complementary to the first part of the nucleic acid molecule as defined in any one of the embodiments of the first aspect;
  b) adding the capture probe and the detection probe separately or combined to a sample containing the nucleic acid molecule as defined in any one of the embodiments of the first aspect or presumed to contain the nucleic acid molecule as defined in any one of the embodiments of the first aspect;
  c) allowing the capture probe and the detection probe to react either simultaneously or in any order sequentially with the nucleic acid molecule as defined in any one of the embodiments of the first aspect or part thereof;
  d) optionally detecting whether or not the capture probe is hybridized to the nucleic acid molecule as defined any one of the embodiments of the first aspect provided in step a); and
  e) detecting the complex formed in step c) consisting of the nucleic acid molecule as defined in any one of the embodiments of the first aspect and the capture probe and the detection probe.

In a second embodiment of the ninth aspect which is also an embodiment of the first embodiment of the ninth aspect, the detection probe comprises a detection means, and/or wherein the capture probe is immobilized to a support, preferably a solid support.

In a third embodiment of the ninth aspect which is also an embodiment of the first and the second embodiment of the ninth aspect, any detection probe which is not part of the complex is removed from the reaction so that in step e) only a detection probe which is part of the complex, is detected.

In a fourth embodiment of the ninth aspect which is also an embodiment of the first, the second and the third embodiment of the ninth aspect, step e) comprises the step of comparing the signal generated by the detection means when the capture probe and the detection probe are hybridized in the presence of the nucleic acid molecule as defined in any one of the embodiments of the first aspect or part thereof, and in the absence of said nucleic acid or part thereof.

The present invention is based on the surprising finding that:
  a) it is possible to generate nucleic acid molecules binding specifically and with high affinity to a lipid, preferably a phospholipid, more preferably S1P;
  b) such nucleic acid molecules, which are nucleic molecules according to the present invention, share a consensus sequence of nucleotides, wherein the consensus sequence of the nucleic acid molecules according to the present invention is preferably essential for the binding charateristics of the nucleic acid molecules according to the present invention, more preferably essential for the binding to S1P;
  c) the binding affinity to a lipid, preferably to a phospholipid, more preferably to S1P of nucleic acid molecules according to the present invention would be improved by replacing a limited number of ribonucleotides by 2'-deoxyribonucleotides.

Such nucleic acids are preferably also referred to herein as the nucleic acid molecules according to the present invention, the nucleic acids according to the present invention, the inventive nucleic acids or the inventive nucleic acid molecules. Insofar, the terms nucleic acid and nucleic acid molecule are used herein in a synonymous manner if not indicated to the contrary.

The features of the nucleic acid according to the present invention as described herein can be realised in any aspect of the present invention where the nucleic acid is used, either alone or in any combination.

The finding that short nucleic acid molecules having high binding affinity, to a lipid, a phospholipid and in particular S1P could be identified, is insofar surprising as no nucleic acid molecules binding to a lipid, a phospholipid and in particular S1P could be identified so far, although nucleic acid molecules directed to almost all target classes such peptides, proteins, nucleic acids, small molecules, antibiotics, amino acids, nucleotides were identified as described in 'The aptamer handbook' (Klussmann, Klussmann, S. (eds.); The Aptamer Handbook, 1. Edition—February 2006, Wiley-VCH, Weinheim). The structure and charge of a lipid, in particular of a phospholipid, explain why the identification of lipid binding nucleic acid molecules has not been successful to date and/or has never been taken into consideration. A phospholipid such as S1P is mainly characterized by its uncharged aliphatic moiety and the one negatively charged phosphate group. Taking the charge and the negative charge of the phosphate group of such lipid into account, it is surprising that the inventors could identify nucleic acid molecules binding to a lipid, and more specifically to a phospholipid. Due to the phosphates in the sugar backbone of nucleic acid molecules, nucleic acid molecules themselves are negatively charged. Therefore, binding of a nucleic acid molecule to another negatively charged molecule or moiety is not very likely. Apart from charge repulsion also seize affects the accessibility of target molecules by nucleic acid molecules having a three-dimensional structure. Altnough several nucleic acid molecules binding to small molecules have been published, generally, nucleic acid molecules against small molecules have affinities in the micromolar range (James, 2000 Encyclopedia of Analytical Chemistry, pp. 4848-4871) which renders them inappropriate for therapeutic use. However, the best S1P binding nucleic acid molecules according to the present invention show high binding affinities, expressed by $K_D$ values, which allow the use of such nucleic acid molecules in vivo, more specifically in a method for treatment or diagnosis of a mammal, preferably man. Preferably the $K_D$ value of the nucleic acid molecules according to the present invention is less than 100 nM, more preferably less than 50 nM. In an embodiment, the nucleic acid molecules according to the invention have a $K_D$ value which is equal to or less than any value defined by the range from 5 to 53 nM. In a further embodiment the nucleic acid molecules according to the invention have an $IC_{50}$ value which is equal to or less than any value defined by the range from 5 to 31 nM.

The nucleic acid molecules according to the present invention bind specifically S1P (also referred to as D-erythro-sphingosine-1-phosphate), but not to D-erythro-sphingosine lackinh the phosphate group.

Because many of the effects of lipids such as of S1P are thought to be mediated by the interaction and more specifically binding of the lipid with one or several lipid receptors, preferably S1P receptors, therapeutic approaches have focussed on targeting lipid receptors, in particular S1P receptors. Thus, it will be acknowledged by the person skilled in the art that the nucleic acid molecules according to the present invention are preferably antagonists of an activity mediated by a lipid, preferably by a phospholipid, more preferably by S1P. Numerous different S1P receptor antagonists and agonists have been identified and described, which, because of their binding to said lipid, have an impact on these lipid mediated activity/activities. They differ in specificity and affinity for the various S1PRs such as $S1P_1$, $S1P_3$, $S1P_4$ and $S1P_5$ and thus display various functional profiles. One of the advantages of nucleic acid molecules according to the present invention is that the nucleic acid molecules according to the present invention are antagonist of S1P and thereby mediate the functions of all S1P receptors rather than addressing and more specifically binding to a single S1P receptor Lipids according to the present invention are, preferably selected from the group, comprising waxes, sterols, fat-soluble vitamins (such as vitamins A, D, E and K), monoglycerides, diglycerides, phospholipids, and others, but not limited thereto.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits or "building blocks": ketoacyl and isoprene groups. Using this approach, lipids may be divided into eight categories: fatty acyls, glycerolipids, glycerophospholipids, sphingolipids, saccharolipids, polyketides (derived from condensation of ketoacyl subunits), sterol lipids and prenol lipids (derived from condensation of isoprene subunits).

Although the term lipid is sometimes used as a synonym for fats, fats are a subgroup of lipids called triglycerides. Lipids also encompass molecules such as fatty acids and their derivatives (including tri-, di-, and monoglycerides and phospholipids), as well as other sterol-containing metabolites such as cholesterol.

Phospholipids are a class of lipids and are a major component of all cell membranes as they can form lipid bilayers. Most phospholipids contain a diglyceride, a phosphate group, and a simple organic molecule such as choline; one exception to this rule is sphingomyelin, which is derived from sphingosine instead of glycerol.

Sphingolipids are a class of lipids derived from the aliphatic amino alcohol sphingosine. The long-chain bases, sometimes simply known as sphingoid bases, are the first non-transient products of de novo sphingolipid synthesis in both yeast and mammals. These compounds, specifically known as phytosphingosine and dihydrosphingosine (also known as sphinganine, although this term is less common), are mainly C18 compounds, with somewhat lower levels of C20 bases. Ceramides and glycosphingolipids are N-acyl derivatives of these compounds. The sphingosine backbone is O-linked to a (usually) charged head group such as ethanolamine, serine, or choline. The backbone is also amide-linked to an acyl group, such as a fatty acid.

Sphingosine 1-phosphate (abbr. S1P) is a 380 Dalton phospholipid with the molecular formula $C_{18}H_{38}NO_5P$. Synonyms of S1P are D-erythro-Sphingosine-1-phosphate,
4-Octadecene-1,3-diol, 2-amino-, 1-(dihydrogen phosphate), (2S,3R,4E)-,
(2S,3R,4E)-2-amino-3-hydroxyoctadec-4-en-1-yl dihydrogen phosphate,
4-Octadecene-1,3-diol, 2-amino-, 1-(dihydrogen phosphate), (R—(R*,S*-(E)))-,
4-Octadecene-1,3-diol, 2-amino-, 1-(dihydrogen phosphate), [R—[R*,S*-(E)]]-,
Sphing-4-enine 1-phosphate,
C18-Sphingosine 1-phosphate,
Sphingosine, D-erythro-1-phosphate,
D-erythro-Dihydrosphingosine 1-phosphate,
(2S,3R,E)-2-Amino-3-hydroxyoctadec-4-enyl dihydrogen phosphate,
(2S,3R,4E)-2-amino-4-octadecene-1,3-diol 1-dihydrogen phosphate),
(2S,3R,4E)-2-ammonio-3-hydroxyoctadec-4-en-1-yl hydrogen phosphate,
(E)-(1S,2R)-2-Hydroxy-1-phosphonooxymethyl-heptadec-3-enyl-ammonium.

The S1P binding nucleic acid molecules of the present inventioncan be characterised in terms of stretches of nucleotides which are also referred to herein as Boxes. The different types of S1P binding nucleic acids comprise different stretches of nucleotides. In general, S1P binding nucleic acid molecules of the present inventioncomprise at their 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily realized in the molecule under physiological and/or non-physiological conditions. The three stretches of nucleotides of S1P binding nucleic acids—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. However, alternatively, the second terminal stretch of nucleotides, the central stretch of nucleotides and the terminal first stretch of nucleotides are arranged to each other in 5'→3'-direction.

The differences in the sequences of the defined boxes or stretches between the different S1P binding nucleic acid molecules influences the binding affinity to S1P. Based on binding analysis of the different S1P binding nucleic acid molecukles of the present invention, the central stretch and their nucleotide sequences as are individually and more preferably in their entirety essential for binding to human S1P.

It is within the present invention that the nucleic acid molecules according to the present invention or stretches thereof or any part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a molecule or a structure formed by two or more separate strands or two spatially separated stretches of a single strand, whereby at least one, preferably two or more base pairs exist which are base-pairing preferably in accordance with the Watson-Crick base pairing rules. It will also be acknowledged by the one skilled in the art that other base pairing such as Hoogsten base pairing may exist in or form such double-stranded structure.

In a preferred embodiment the term arrangement as used herein, means the order or sequence of structural or functional features or elements described herein in connection with the nucleic acid molecules disclosed herein.

It will be acknowledged by the person skilled in the art that the nucleic acid molecules according to the present invention are capable of binding of the molecules of the present invention to S1P. Without wishing to be bound by any theory, the present inventors assume that the S1P binding results from a combination of three-dimensional structural traits or elements of the individual nucleic acid molecule, which are caused by orientation and folding patterns of the sequence of nucleotides forming such traits or elements, whereby preferably such traits or elements are the first terminal stretch of nucleotides, the central stretch of nucleotides and for the second terminal stretch of nucleotides of the S1P binding nucleic acid molecules. It is evident that the individual trait or element may thus be formed by various different individual sequences the degree of variation of which may vary depending on the three-dimensional structure such element or trait has to form. The overall binding characteristic of the nucleic acid molecule results from the interplay of the various elements and traits, respectively, which ultimately results in the interaction and more specifically binding of the nucleic acid molecule with its target, i.e. S1P. Again without wishing to be bound by any theory, the central stretch that is characteristic for S1P binding nucleic acid moleculess of the present invention seems to be important for mediating and/or establishing the binding of the claimed nucleic acid with S1P. Substantially the nucleic acid molecules according to the present invention are suitable for the detection of S1P. Also, it will be acknowledged by the person skilled in the art that the nucleic acid molecules according to the present invention are antagonists of an activity mediated by the S1P Because of this the nucleic acid molecules according to the present invention are suitable for the treatment and prevention, respectively, of any disease which is associated with or caused by either S1P. The scientific rational may be taken from the prior art which establishes that S1P is involved or associated with a variety of diseases and conditions, respectively, and which is incorporated herein by reference.

The nucleic acid molecules according to the present invention shall also comprise nucleic acid molecules which are substantially homologous to the particular sequences, and preferably the particular sequences of the nucleic acid molecules according to the present invention disclosed herein. The term substantially homologous shall be understood such that the homology is at least 75%, preferably 85%, more preferably 90% and most preferably more than 95%, 96%, 97%, 98% or 99%.

The actual percentage of homologous nucleotides present in the nucleic acid molecule according to the present invention relative to a reference nucleotide sequence or reference nucleic acid molecule according to the present invention will depend on the total number of nucleotides present in the nucleic acid molecule. The percent modification can be based upon the total number of nucleotides present in the nucleic acid molecule. Preferably, the homologous nucleotides of the nucleic acid molecule of the present invention are selected from the group comprising ribonucleotides and 2'-deoxyribonucleotides.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any SEQ.ID.No 12, 18, 36, 41 and 42.

Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al., 2004). The nucleic acid molecule according to the present invention shall also comprise those nucleic acid molecules comprising one or several of the nucleic acid sequences disclosed herein or part thereof, preferably to the extent that the nucleic acid molecules or said parts are involved in the binding to human S1P. Such nucleic acid molecule is, in an embodiment, one of the nucleic acid molecules described herein, or a derivative and/or a metabolite thereof, whereby such derivative and/or metabolite are preferably a truncated nucleic acid molecule compared to the nucleic acid molecules described herein. Truncation may be related to either or both of the ends of the nucleic acid molecules as disclosed herein. Also, truncation may be related to the inner sequence of nucleotides of the nucleic acid molecule, i.e. it may be related to the nucleotide(s) between the 5' and the 3' terminal nucleotide, respectively. Moreover, truncation shall comprise the deletion of as little as a single nucleotide from the sequence of the nucleic acid molecule s disclosed herein. Truncation may also be related to one or more than one stretch of the nucleic acid molecule(s) of the present invention, whereby the stretch can be as little as one nucleotide long.

The binding of a nucleic acid molecule according to the present invention can be determined by the ones skilled in the art molecule using routine experiments or by using or adopting a method as described herein, preferably as described herein in the example part.

The nucleic acid molecules according to the present invention may be either D-nucleic acid molecules (D-nucleic acid molecules) or L-nucleic acids (L-nucleic acid molecules). Preferably, the nucleic acids are L-nucleic acid molecules. In addition, it is possible that one or several parts of the nucleic acid molecule are present as D-nucleic acids or at least one or several parts of the nucleic acids are L-nucleic acids. The term "part" of the nucleic acids molecule shall mean as little as one nucleotide. Such nucleic acid molecules are generally referred to herein as D- and L-nucleic acids, respectively. Therefore, in a particularly preferred embodiment, the nucleic acid molecules according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid molecule is involved. Preferably, such D-nucleotide is attached at a terminus of any of the stretches and of any nucleic acid molecule according to the present invention, respectively. In a further preferred embodiment, such D-nucleotides may act as a spacer or a linker, preferably attaching modifications or modification groups, such as PEG and HES to the nucleic acids according to the present invention.

It is also an embodiment of the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acid molecules according to the present invention are part of a longer nucleic acid molecule whereby this longer nucleic acid comprises several parts whereby at least one such part is a nucleic acid molecule according to the present invention, or a part thereof. The other part(s) of these longer nucleic acid molecules can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to S1P. One possible function is to allow interaction with one or other molecules, whereby such one or other molecules preferably are different from S1P, such as, e.g., for immobilization, cross-linking, detection or amplification. In a further embodiment of the present invention the nucleic acid molecules according to the invention comprise, as individual or combined moieties, several of the nucleic acid molecules of the present invention. Such nucleic acid moleculecomprising several of the nucleic acid molecules of the present invention is also encompassed by the term longer nucleic acid molecule.

L-nucleic acids or L-nucleic acid molecules as used herein are nucleic acids consisting of L-nucleotides, preferably consisting completely of L-nucleotides.

D-nucleic acids or D-nucleic acid molecules as used herein are nucleic acids consisting of D-nucleotides, preferably consisting completely of D-nucleotides.

Also, if not indicated to the contrary, any nucleotide sequence is set forth herein in 5'→3' direction.

As preferably used herein any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the seond nucleotide counted from the 3' end of a sequence, stretch and substretch, respectively.

Irrespective of whether the nucleic acid molecule of the present invention consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the nucleic acid molecules according to the present invention as L-nucleic acid molecule s advantageous for several reasons. L-nucleic acid molecules are enantiomers of naturally occurring nucleic acid molecules. D-nucleic acid molecules, however, are not very stable in aqueous solutions and particularly in biological systems or biological samples due to the widespread presence of nucleases. Naturally occurring nucleases, particularly nucleases from animal cells are not capable of degrading L-nucleic acid molecules. Because of this the biological half-life of the L-nucleic acid moleculeis significantly increased in such a system, including the animal and human body. Due to the lacking degradability of L-nucleic acid no nuclease degradation products are generated from such L-nucleic acid molecule and thus no side effects arising therefrom observed. This aspect delimits the L-nucleic acid molecule of factually all other compounds which are used in the treatment of diseases and/or disorders involving or being mediated by S1P. L-nucleic acid molecules which specifically bind to a target molecule through a mechanism different from Watson Crick base pairing, or aptamers which consists partially or completely of L-nucleotides, particularly with those parts of the aptamer being involved in the binding of the aptamer to the target molecule, are also called Spiegelmers.

It is also within the present invention that the inventive nucleic acid molecule of the present inventions, regardless whether they are present as D-nucleic acids, L-nucleic acids or D, L-nucleic acids or whether they are DNA or RNA, may be present as single-stranded or double-stranded nucleic acids. Typically, the nucleic acids molecules according to the present invention are single-stranded nucleic acids which exhibit defined secondary structures due to the primary sequence and may thus also form tertiary structures. The nucleic acids molecules according to the present invention, however, may also be double-stranded in the meaning that two strands which are complementary or partially complementary to each other are hybridised to each other. This confers stability to the nucleic acid molecule which, in particular, will be advantageous if the nucleic acid molecule is present in the naturally occurring D-form rather than the L-form.

The nucleic acid molecules of the present invention may be modified. Such modifications may be related to the single nucleotide of the nucleic acid moleculeand are well known in the art. Examples for such modification are described in, among others, Venkatesan (2003); Kusser (2000); Aurup (1994); Cummins (1995); Eaton (1995); Green (1995); Kawasaki (1993); Lesnik (1993); and Miller (1993). Such modification can be a H atom, a F atom or O—CH3 group or NH2-group at the 2' position of the individual nucleotide of which the nucleic acid molecule consists. Also, the nucleic acid molecule according to the present invention can comprise at least one LNA nucleotide. In an embodiment the nucleic acid molecule according to the present invention consists of LNA nucleotides.

The present inventors surprisingly found that non-chemical modificactions or substitutions in a S1P binding RNA molecule of the present invention, i.e. an L-nucleic acid molecule of the present invention consisting of L-ribonucleotides, lead to an improved binding affinity of the S1P binding RNA molecule of the present invention in comparison to the parent S1P binding RNA nucleic acid molecule according to the present invention, i.e. a nucleic acid molecule of the present invention consisting of ribonucleotides, without such non-chemical modificaction(s) or substitution(s). The non-chemical modification or substitions are preferably selected from the group of replacingone or more L-ribonucleotide(s) in an RNA nucleic acid molecule according to the present invention, i.e. a nucleic acid molecule of the present invention consisting of ribonucleotides by one or more L-deoxyribonucleotide(s).

In a preferred embodiment binding affinity of an S1P binding nucleic acid—the RNA spiegelmer L-S1P-215-F9-002 solely consisting of ribonucleotides—was improved by replacing up to five ribonucleotides by up to five deoxyribonucleotides, preferably by replacing four ribonucleotides by four deoxyribonucleotides.

In an embodiment, the nucleic acid molecule according to the present invention may be a multipartite nucleic acid. A multipartite nucleic acid molecule as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acid molecule s by either cleaving the nucleic acid to generate two strands or by synthesising one nucleic acid corresponding to a first part of the inventive, i.e. overall nucleic acid molecule and another nucleic acid corresponding to the second part of the overall nucleic acid molecule. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

Finally it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable $K_D$ value range.

A possibility to determine the binding constants of the nucleic acid molecules according to the present invention is the use of surface plasmon resonance as described in example 4 and 6 which confirms the above finding that the nucleic acids according to the present invention exhibit a favourable $K_D$ value range. An appropriate measure in order to express the intensity of the binding between the individual nucleic acid molecule and to the target which is in the present case S1P, is the so-called $K_D$ value which as such as well the method for its determination are known to the one skilled in the art.

The nucleic acids according to the present invention are characterized by a certain $K_D$ value. Preferably, the $K_D$ value shown by the nucleic acids according to the present invention is below 1 µM. A $K_D$ value of about 1 µM is said to be characteristic for a non-specific binding of a nucleic acid to a target. As will be acknowledged by the ones in the art, the $K_D$ value of a group of compounds such as the nucleic acids according to the present invention are within a certain range. The above-mentioned $K_D$ of about 1 µM is a preferred upper limit for the $K_D$ value. The preferred lower limit for the $K_D$ of target binding nucleic acids can be about 10 picomolar or higher. It is within the present invention that the $K_D$ values of individual nucleic acids binding to S1P is preferably within this range. Preferred ranges can be defined by choosing any first number within this range and any second number within this range. Preferred upper values are 250 nM and 100 nM, preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. The modifications such as linear poly(ethylene)glycol, branched poly(ethylene)glycol, hydroxyethyl starch, a peptide, a protein, a polysaccharide, a sterol, polyoxypropylene, polyoxyamidate, poly (2-hydroxyethyl)-L-glutamine and polyethylene glycol as well as the process of modifying a nucleic acid using such modifications, is described in European patent application EP 1 306 382, the disclosure of which is herewith incorporated in its entirety by reference.

In the case of PEG being such high molecular weight moiety the molecular weight is preferably about 20,000 to about 120,000 Da, more preferably from about 30,000 to about 80,000 Da and most preferably about 40,000 Da. In the case of HES being such high molecular weight moiety the molecular weight is preferably from about 50 to about 1000 kDa, more preferably from about 100 to about 700 kDa and most preferably from 200 to 500 kDa. HES exhibits a molar substitution of 0.1 to 1.5, more preferably of 1 to 1.5 and exhibits a substitution sample expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in the patent applications WO2005074993 and WO2003035665.

In a preferred embodiment the linker is a biodegradable linker. The biodegradable linker allows to modify the characteristics of the nucleic acid according to the present invention in terms of, among other, residence time in the animal body, preferably in the human body, due to release of the modification from the nucleic acid according to the present invention. Usage of a biodegradable linker may allow a better control of the residence time of the nucleic acid according to the present invention. A preferably embodiment of such biodegradable linker are biodegradable linker as described in but not limited to the international patent applications WO2006/052790, WO2008/034122, WO2004/092191 and WO2005/099768, whereby in the international patent applications WO2004/092191 and WO2005/099768, the linker is part of a polymeric oligonucleotide prodrug that consists of one or two modifications as described herein, a nucleic acid molecule and the biodegradable linker in between.

It is within the present invention that the modification or modification group is a biodegradable modification, whereby the biodegradable modification can be attached to the nucleic acid molecule of the present invention either directly or through a linker. The biodegradable modification allows to modify the characteristics of the nucleic acid according to the present invention in terms of, among other, residence time in the animal body, preferably in the human body, due to release of the modification from the nucleic acid according to the present invention. Usage of biodegradable modification may allow a better control of the residence time of the nucleic acid according to the present invention. A preferably embodiment of such biodegradable modification is biodegradable as described in but not restricted to the international patent applications WO2002/065963, WO2003/070823, WO2004/113394 and WO2000/41647, in WO2000/41647 preferably page 18, line 4 to 24.

Beside the modifications as described supra, other modifications can be used to modify the characteristics of the nucleic acids according to the present invention, whereby such modifications are selected from the group of proteins, lipids such as cholesterol and sugar chains such as amylase, dextran etc.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that, despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation. Insofar, the modification(s) of the nucleic acid molecules as disclosed herein and the thus modified nucleic acid molecules and any composition comprising the same may provide for a distinct, preferably controlled pharmacokinetics and biodistribution thereof. This also includes residence time in circulation and distribution to tissues. Such modifications are further described in the patent application WO2003035665.

However, it is also within the present invention that the nucleic acids disclosed herein do not comprise any modification and particularly no high molecular weight modification such as PEGylation or HESylation. Such embodiment is particularly preferred when the nucleic acid shows preferential distribution to any target organ or tissue in the body or when a fast clearance of the nucleic acids from the body after administration is desired. Nucleic acids as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids as disclosed herein from the body after administration might be desired in case of in vivo imaging or specific therapeutic dosing requirements using the nucleic acids or medicaments comprising the same, each according to the present invention.

The inventive nucleic acids, which are also referred to herein as the nucleic acids according to the present invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of S1P in the respective pathogenetic mechanism.

The present invention provides a means to neutralize S1P by identification and use of S1P binding nucleic acid. Because the nucleic acids according to the present invention interact with human and animal S1P, a skilled person is expected to understand that the S1P binding nucleic acid of the present invention can be used for the treatment, prevention and/or diagnosis of any disease of humans and animals described herein. In connection therewith, it is to be acknowledged that the nucleic acids of the present invention can be used for the treatment and prevention of diseases, disorders, or conditions described herein, irrespective of the mode of action underlying such disease, disorder, or condition.

In the following, and without wishing to be bound by any theory, the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the S1P and its receptors $S1P_1$, $S1P_2$, $S1P_3$, $S1P_4$ and $S1P_5$ as outlined in connection therewith said interaction may be addressed by the nucleic acid molecules according to the present invention such that the claimed therapeutic, preventive and diagnostic effect is achieved. It should furthermore be acknowledged that the particularities of the disease, disorders and conditions, of the patients and any detail of the treatment regimen described in connection therewith, may be subject to preferred embodiments of the instant application.

The indications, diseases and disorders for the treatment and/or prevention of which the nucleic acids molecules, the pharmaceutical compositions and medicaments in accordance with or prepared in accordance with the present invention result from the involvement, either direct or indirect, of S1P in the respective pathogenetic mechanism. Neutralization of S1P might be beneficial in diseases and conditions that are, at least in part, characterized by one or more pathological processes regulated by S1P, such as hyperproliferation, aberrant neovascularization, angiogenesis, fibrogenesis, fibrosis, scarring, abberrant cell trafficking, abberant vascular integrity, inflammation, and autoimmune response. The classifications provided herein are for descriptive convenience and do not limit the invention.

S1P promotes cell growth by stimulating cell proliferation and survival. As such, decreasing the effective in vivo concentrations of S1P is expected to be beneficial in treating or preventing hyperproliferative disorders. Hyperproliferative disorders are defined as disease and/or disorders and/or diseased conditions associated with an uncontrolled proliferation of cells. S1P-associated hyperproliferative disorders including hyperplasias, neoplasias, disorders associated with endothelial cell proliferation and disorders associated with fibroblast proliferation. In most cases the neoplasia will be a cancer.

Hyperproliferative disorders associated with endothelial cells can result in diseases of angiogenesis. Examples for such diseases and conditions are cancers caused by solid tumors or hematological tumors, angiomas, endometriosis, obesity, age-related macular degeneration, and various retinopathies, as well as the proliferation of endothelial cells and smooth muscle cells that cause restenosis as a consequence of stenting in the treatment of atherosclerosis.

A growing body of evidence implicates S1P as a highly potent proangiogenic agent. S1P stimulates chemotactic motility of human venous endothelial cells (HUVECs) and induces differentiation of multicellular structures [Liu et al., J Clin Invest. 2000 106:951-961] and promotes migration of EC precursors to neovascularization sites [Annabi, Exp Hematol. 2003 July; 31(7):640-9]. In a recent study with a murine anti-S1P antibody, it was shown in different in vitro assays that S1P neutralization with the antibody inhibited cytoprotective effects and the migration of vascular endothelial cells. In in vivo studies the same antibody inhibited VEGF induced angiogenesis in a matrigel plug assay in mice as well as the release of proangiogenic cytokines, such as VEGF, bFGF, IL-6, and IL-8 from tumor cells. In xenografted mice carrying human cancer cells, the treatment with the murine anti-S1P antibody significantly slowed tumor progression [Visentin, Cancer Cell. 2006 March; 9(3):225-38]. Thus, an agent that directly binds to and neutralizes S1P is useful to counter S1P mediated effects in the treatment of proangiogenic activity in pathologic conditions including but not limited to cancer and ocular diseases associated with retinal and choroidal neovascularization (Caballero, Exp Eye Res 2009, 88: 367-377; Skoura, J Clin Invest 2007, 117: 2506-2516;Xie, J Cell Physiol 2009, 218: 192-198) such as age-related macular degeneration.

Hyperproliferative disorders involving fibroblasts include but are not limited to disorders of excessive scarring (for example, fibrosis) such as age-related macular degeneration [Caballero, Exp Eye Res. 2009 March; 88(3):367-77], cardiac remodeling and failure associated with myocardial infarction [Takuwa Cardiovasc Res. 2010 Feb. 1; 85(3):484-93], scleroderma [Bu, Arthritis Rheum. 2010 July; 62(7):2117-26], cystic fibrosis [Uhlig, Am J Respir Crit. Care Med. 2008 Dec. 1; 178(11):1100-14], and excessive wound healing such as commonly occurs as a consequence of surgery or injury, keloids, and fibroid tumors and stenting.

S1P activates fibroblast migration, proliferation and stimulates their production of collagen. Thus, upon cellular injury and/or inflammation, S1P produced locally by damaged cells could be responsible for aberrant wound healing, fibrogenesis and fibrosis. Thus, an agent that directly binds to and neutralizes S1P is useful to counter S1P-mediated effects in the treatment of diseases and conditions associated with an excessive activity or number of fibroblasts including but not limited to ocular diseases such as age-related macular degeneration, cardiovascular diseases, and scleroderma.

S1P regulates motility, adhesion and trafficking of lymphocytes. The egress of lymphocytes from lymphoid tissues is believed to follow a S1Pn gradient with low S1P concentrations in the tissue and high S1P concentrations in the circulation. This perception is supported by studies showing that inhibition of the S1P-degrading enzyme S1P lyase results in lymphopenia [Schwab, Science 2005, 309(5741):1735-9]. They drug FTY720 (fingolimod) causes lymphopenia by acting on S1P receptors and has successfully been used in transplantation and autoimmune diseases (Japtok and Kleuser, Curr Opin Investig Drugs. 2009 November; 10(11):1183-94). In addition to lymphocytes, S1P also stimulates migration, proliferation and survival of other immune cells, such as neutrophils, mast cells and dendritic cells as well as of fibroblasts, epithelial cells, pericytes and other cell types, by these means regulating neovascularization and vascular permeability [Annabi, Exp Hematol. 2003 July; 31(7):640-9; Paik, Genes Dev. 2004 Oct. 1; 18(19):2392-403; Chae, J Clin Invest 2004, 114, 1082-9]. Thus, decreasing the effective plasma concentration of a particular target lipid in vivo, for example, S1P by a neutralizing agent, such as a S1P binding nucleic acid molecule may be used to direct effector T lymphocytes away from inflammation sites thereby being useful in the treatment of diseases including but not limited to autoimmune disease and ocular diseases with inflammatory components, such as choroidal neovascularization seen in age-related macular degeneration.

S1P plays an important role in regulation of endothelial and epithelial barriers [Marsolais and Rosen, Nat Rev Drug Discov, 2009 April; 8(4):297-307]. The vascular endothelial cell barrier separates the vascular components from the interstitium. Disruption of these barriers causes a higher vascular permeability leading to inflammation and affecting the organ function. S1P maintains the integrity of the barrier. This is thought to be mediated primarily by its interaction with S1P1 [Singleton, FASEB J. 2005 October; 19(12):1646-56; Freistritzer and Riewald, Blood. 2005 Apr. 15; 105(8):3178-84], although other S1PR may be involved as well. Antagonism of S1P1 was shown to induce vascular leakage [Sanna et al., Nat Chem. Biol. 2006 August; 2(8):434-41] and there is evidence that the balance between S1P1 and S1P2 is important in the S1P mediated regulation of vascular permeability. Under normal circumstances it may be important to maintain the integrity of the endothelial and epithelial barriers and increased vascular permeability contributes to in acute lung injury and sepsis [Wang, Microvasc Res., 2009 January; 77(1):39-45.]. On the other hand there may be diseases or pathological situations where a temporary disruption of such barrier is desirable or beneficial. In neoplastic diseases, vascular stabilization is important for neoangiogenesis and tumor metastasis [Paik, Genes Dev. 2004 Oct. 1; 18(19):2392-403]. Reducing the expression of S1P1 by siRNA suppressed vascular stabilization in tumor xenograft models resulting in a dramatic suppression of tumor growth [Chae, J Clin Invest 2004, 114, 1082-9]. Functional S1P receptor antagonist FTY720 has been shown to inhibit VEGF-induced vascular permeability, tumor vascularization and growth in a murine melanoma model [LaMontagne, Cancer Res. 2006 Jan. 1; 66(1):221-31]. Furthermore, the transient direct neutralization of S1P may be beneficial in conditions where the disruption of endothelial or epithelial barrier is useful to treat a pathological state, either on its own or in combination with one or more additional therapeutic medication(s), whose effect(s) or treatment of a pathological state may be enhanced by such disruption of the barrier. The effect of an agent that directly interferes with S1P itself and thus blocks the activation of all extracellular S1P receptors on vascular permeability has not been shown yet. It remains subject of speculation whether vascular permeability is increased or decreased. Both may be useful for the treatment of diseases as laid out above.

Due to the involvement of bioactive lipids in various pathological processes including hyperproliferation, neovascularization, angiogenesis, aberrant fibrogenesis, inflammation and vascular stability, decreasing the effective in vivo concentration of S1P through direct interaction with a neutralizing agent, such as an S1P binding nucleic acid molecules may therefore be relevant for treating pathological conditions in which S1P may cause or contribute to the condition. Such diseases and conditions may be systemic or localized to one or more specific body systems, parts or organs. Classes of diseases or disorders amenable to treatment by such methods include but are not limited to cancer, infection and inflammation, autoimmune disorders, cerebrovascular diseases, cardiovascular diseases, ocular diseases, scarring, ventilation-induced lung injury, skin diseases, diseases or disorders associated with excessive fibrogenesis and fibrosis, diseases or disorders associated with pathologic angiogenesis, diseases or disorders associated with aberrant neovascularization,diseases or disorders associated with aberrant vascular stability, and diseases or disorders associated with transplantations as described in greater detail below.

Cancer cells often escape from therapeutic regimes by constantly mutating and evolving, thus becoming resistant to cytotoxics or antiangiogenic agents. An important mechanism how cancer cells become resistant to treatment is the up-regulation of sphingosine kinase 1 (SphK 1) and in turn the release of S1P into the tumor microenvironment [Raguz, Br J Cancer 2008, 99: 387-3912008; Cuvillier, Curr Mol Pharmacol 2010, 3: 53-65). A possible mechanism of S1P-mediated chemoresistance involves a cross-talk between S1P and hypoxia-inducible transcription factor (HIF) where the response of cancer cells to hypoxia involves the up-regulation of the S1P/SphK system [Ader, Cancer Res 2009, 68: 8635-8642]. Taken together, it may be a promising approach to overcome drug resistance linked with S1P overproduction with S1P-neutralizing agents, such as S1P-binding nucleic acid molecules.

Various processes regulated by S1P such as aberrant angiogenesis/neovascularization, aberrant remodeling, fibrosis, scarring and inflammation occur in association with ocular diseases [Eichler, et al. (2006), Curr Pharm Des, vol 12: 2645-60].

Age-related macular degeneration (AMD) is the leading cause of blindness in the western world in patients over age 60 [Bylsma and Guymer (2005), Clin Exp Optom, vol 88: 322-34, Gryziewicz (2005), Adv Drug Deliv Rev, vol 57: 2092-8, and Liu and Regillo (2004), Curr Opin Ophthalmol, vol 15: 221-6.]. Even though the exact etiology of AMD is not fully understood, various S1P-regulated processes such as choroidal neovascularization (CNV), sub-retinal fibrosis, edema and inflammation contribute to the pathogenesis of AMD and AMD-related visual loss [Tezel and Kaplan (2004), Trends MoI Med, vol 10: 417-20, and Ambati, et al. (2003), Sury Ophthalmol, vol 48: 257-93]. VEGF contributes to the pathogenesis of AMD by increasing CNV and vascular permeability which results in the occurrence of intra- and subretinal edema. Thus, current therapy focuses on the inhibition of VEGF by intravitreal injection of anti-VEGF monoclonal antibody. Growing evidence suggests a role for S1P in exudative (i.e. wet) AMD-associated CNV, fibrosis and inflammation. S1P induces the recruitment of epithelial cells to the site of vascularisation and stimulates the generation of early blood vessel structures [Lee, Biochem Biophys Res Commun 1999, 264: 743-750] and it promotes the formation of N-cadherin-mediated junctions between epithelial cells and mural cells in an VEGF-independent manner [Paik, Genes Dev. 2004 Oct. 1; 18(19):2392-403]. S1P furthermore supports neovascularization by cross-activating other pro-angiogenic factors, such as bFGF and VEGF [Igarashi, Proc Natl Acad Sci USA 2003, 100: 10664-9]. Cross-talk of S1P with pro-fibrotic factors, such as TGFb, PDGF and connective tissue growth factor and the induction through S1P of collagen expression by retinal pigmented epithelial cells strongly suggests a role of S1P in AMD-associated fibrogenesis [Xin, J Biol Chem 2004, 279: 35255-35262; Hobson, Science 2001, 291: 1800-1803; Katsuma, FEBS Lett 2005, 579: 2576-2582; Swaney, Exp Eye Res 2008, 87: 367-375]. In addition, there is accumulating evidence that S1P-mediated inflammatory events contribute to the pathogenesis of AMD. Systemic depletion of macrophages attenuated laser-induced CNV [Sakurai, Invest Ophthalmol Vis Sci 2003, 44: 3578-3585] and neutralizing anti-S1P antibody reduced macrophage infiltration [Xie, J Cell Physiol 2009, 218: 192-198]. Furthermore S1P has been implicated as a major downstream mediator of C5a action [Vlasenko, J Immunol 2005, 174: 6456-6461] suggesting that the C5a-S1P-axis could be critically involved in ocular inflammatory processes as they occur for example during AMD. In agreement with these data, intravitreal injection of a neutralizing anti-S1P antibody blocked CNV formation and sub-retinal fibrosis after laser-induced disruption of Bruch's membrane, a model of exudative AMD [Caballero, Exp Eye Res 2009, 88: 367-377; O'Brien, J Lipid Res 2009, 50: 2245-2257]. Furthermore, in a single dose Phase Ia clinical trial, the S1P neutralizing antibody lead to regression of neovasculature in some patients, an effect that has not been seen with anti-VEGF therapies after a single dose [Sabbadini, Br J. Pharmacol. 2011 March; 162(6):1225-38]. Taken together, there is compelling evidence that a neutralizing agent reducing the intravitreal concentrations of S1P, such as an S1P binding nucleic acid molecule, will be a promising approach for the treatment of exudative AMD and other ocular diseases associated with neovascularisation, fibrosis and inflammation.

Diabetic retinopathy (DR) is a common complication in patients with diabetes. DR is an ischemic retinopathy, thus characterized by compromised retinal blood flow. The pathology of DR involves VEGF-driven retinal neovascularization which can ultimately lead to intraocular hemorrhaging, fractional retinal detachment and increased vascular permeability. The role of S1P in neovascularization, vascular permeability and fibrosis has suggested that antagonizing S1P could be beneficial for the treatment of DR. Indeed, inhibition of S1P formation by small-molecule antagonists of SPHK attenuated early events of VEGF-induced vascularization and retinal vascular leakage in streptozotocin-induced diabetic retinopathy in rats [Maines, Invest Ophthalmol Vis Sci 2006, 47: 5022-5031]. One of the major causes of visual impairment in patients with diabetic retinopathy is the development of diabetic macular edema (DME). VEGF-induced neovascularization and vascular leakage is extensively involved in DME development and progression [Aiello, Diabetes 1997, 46: 1473-1480]. Accordingly, anti-VEGF antibody (ranibizumab, Lucentis) treatment has been successfull in DME [Massin, Diabetes Care. 2010, 33(11):2399-405] and has recently received approval. Given the inhibitory effects of neutralizing anti-S1P antibody on VEGF-mediated neovascularization and vascular leakage [LaMontagne, Cancer Res. 2006 Jan. 1; 66(1):221-31; Visentin, Cancer Cell. 2006 March; 9(3):225-38] it is expected that a neutralizing agent reducing the intravitreal and retinal concentrations of S1P, such as a S1P binding nucleic acid molecule, will be a promising approach for the treatment of DME.

Retinal Pigment Epithelium (RPE) detachment occurs secondary to ocular diseases associated with neovascularization, increased vascular permeability and stimulation of fibrogenesis, such as AMD and DR. S1P is strongly upregulated by RPE upon laser-induced injury [Caballero, Exp Eye Res 2009, 88: 367-377]. Evidence for a beneficial effect of antagonizing S1P in RPE detachment is provided by a clinical phase 1 trial of monoclonal anti-S1P antibody sonepcizumab. Patients with occult disease experienced a resolution of RPE detachment, an effect that has not been investigated for anti-VEGF treatment [Sabbadini, Br J. Pharmacol. 2011 March; 162(6): 1225-38].

Proliferative vitreoretinopathy (PVR) is the most common complication of a retinal detachment. PVR pathophysiology finally results in excessive scarring of the retina. Given the described cross-talk between S1P and growth factor such as VEGF, bFGF, IL-6, and IL-8 and the inhibitory effect of neutralizing anti-S1P antibody on these factors [Visentin, Cancer Cell 2006, vol 9: 1-14; Milstien and Spiegel, Cancer Cell 2006, vol 9: 148-150]. Given the pathophysiology that ultimately results in the excessive scarring seen in PVR and the known effects of functional S1P receptor antagonist FTY720 on these same key mediators as well as the curative effects of sonepcizumab in patients with retinal detachment [Sabbadini, Br J. Pharmacol. 2011 March; 162(6):1225-38], it is expected that a neutralizing agent reducing the intravitreal concentrations of S1P, such as a S1P binding nucleic acid molecule, will be a promising approach for the treatment of PVR.

Retinal fibrosis leads to irreversible damage of photoreceptors and visual loss in AMD and DR. This process is not addressed by currently available treatments. Neutralizing anti-S1P antibody blocked CNV formation and sub-retinal fibrosis in laser-induced disruption of Bruch's membrane, a model of exudative AMD [Caballero, Exp Eye Res 2009, 88: 367-377].

In a model of retinopathy of prematurity (ROP) S1P2-deficient mice showed a reduction in pathologic neovascularization in the vitreous chamber [Skoura, J Clin Invest 2007, 117: 2506-2516]. Neutralizing anti-S1P antibody effectively blocked retinal neovascularization and vascular leakiness in the ROP model of ischemia-induced angiogenesis [Xie, J Cell Physiol 2009 218: 192-198]. Neutralizing anti-S1P antibody could furthermore limit the infiltration of macrophages during ROP [Xie, J Cell Physiol 2009, 218: 192-198].

Elevated intraocular pressure is the main risk-factor in glaucoma. S1P was shown to decrease outflow facility in porcine and human eyes, thus increasing outflow resistance and intraocular pressure [Mettu, Invest Ophthalmol Vis Sci. 2004 July; 45(7):2263-71; Stamer, Exp Eye Res. 2009 December; 89(6):980-8]. S1P2 receptor activation increases conventional outflow resistance [Sumida, Am J Physiol Cell Physiol. 2011 Feb. 2]. Thus, reducing the intravitreal concentrations of S1P by a neutralizing agent, such as a S1P binding nucleic acid molecule, will be a promising approach for the treatment of glaucoma.

Given the known pleotropic effects of S1P and its interactions with VEGF and related growth factors and cytokines it is anticipated that reducing the effective ocular concentration of S1P will be effective at suppressing ischemic retinopathies associated with VEGF-driven proliferation of pathological retinal neovascularization. These include but are not limited to sickle cell retinopathy, retinal venous occlusive disease, macular puckers (cellophane retinopathy), proliferative diabetic retinopathy (PDR), and retinal neovascular diseases.

Other ocular conditions characterized, at least in part, by aberrant neovascularization or angiogenesis include contact lens overwear, infections of the cornea, including herpes simplex, herpes zoster and protozoan infection, pterygium, infectious uveitis, lymphangiogenesis after corneal transplantation and transplant rejection, chronic retinal detachment, complications of refractive surgery such as haze, stromal scarring and regression, sickle cell retinopathy, venous occlusive disease, retinal angiomatous proliferation, and idiopathic polypoidal choroidal vasculopathy.

Other ocular diseases with an inflammatory or immune component include chronic vitritis, autoimmune uveoretinits, allergic conjunctivitis, vernal conjunctivitis, herpes simplex, herpes zoster, and protozoan infections [Ciulla, et al. (2001), Curr Opin Ophthalmol, vol 12: 442-9], and ocular histoplasmosis.

S1P is involved in the regulation of scarring. Scarring of the anterior portion of the eye is involved in trauma (resulting from various hazards ranging from airborne debris to blunt trauma that can for example result from surgery, and chemicals) [Dart et al (2003), Eye, vol 17: 886-92], Ocular Cicatricial Pemphigoid (OCP) (a chronic cicatrizing (scar-forming) autoimmune disease that primarily affects the conjunctiva), Stevens Johnson Syndrome (SJS), and Toxic Epidermal Necrolysis (TEN) (life-threatening adverse reactions to medications), Pterygium (a winglike triangular membrane that occurs in the interpalpebral fissure that can result in visual loss; VEGF may play an important role in the development of pterygium [Dougherty, et al. (1996), Cornea, vol 15: 537-540, and Lee, et al. (2001), Cornea, vol 20: 238-42])

S1P promotes hyperproliferation during hyperplasia and neoplasia by stimulating cell proliferation and protecting from apoptosis.

Neoplasia refers to abnormal, uncontrolled and disorganized cell growth. In most cases neoplasia will be cancer. Several lines of evidence suggest that it is the balance of S1P in relation to sphingosine and ceramide that determines cell fate [Morita et al., 2000, Melendez and Khaw, 2002; Baumruker and Prieschl, 2000]. Cancer cells have been shown to up-regulate SPHK1 thereby increasing the S1P concentrations in the tumor microenvironment [Pyne, Nat Rev Cancer 2010, 10: 489-503]. Decreasing SPHK1 expression induces cell cycle arrest and apoptosis in breast cancer cells and small molecule inhibitors of SPHK reduced tumor growth in models of mammary adenocarcinoma, histocytic leukemia, glioblastoma xenografts, and AML xenografts [Sabbadini, Br J. Pharmacol. 2011 March; 162(6):1225-38].

In agreement with these results from animal models SPHK was over-expressed in patients with solid tumors, among others those of breast, colon, lung, ovary, stomach, uterus, kidney, prostate, and rectum [French, et al., Cancer Res 63: 5962-5969, 2003; Fyrst, Nat Chemical Biology 2010, 489-497]. Increased expression of SPHK correlates with a significant decrease in survival rates in patients with several forms of cancer [Sabbadini, Br J. Pharmacol. 2011 March; 162(6): 1225-38]. S1P neutralizing antibodies were shown to inhibit the proliferation of cancerous cell lines, their invasiveness and their resistance to doxorobucin-induced apoptosis in vitro, i.e. A549, HT-29, MCF-7 cells [Visentin, Cancer Cell. 2006 March; 9(3):225-38].

In addition to its hyperproliferative effects, S1P promotes neovascularization, angiogenesis and metastasis, which are crucial processes in cancer pathology. A growing body of recent evidence implicating S1P as one of the most potent pro-angiogenic agents comes from studies directly comparing S1P with agents such as VEGF and bFGF. S1P stimulates DNA synthesis and chemotactic motility of human venous endothelial cells (HUVECs), while inducing differentiation of multicellular structures, all of which is suggestive of S1P's role in early blood-vessel formation (Argraves, et al., 2004; Lee et al., 1999; Liu et al., J Clin Invest. 2000 106:951-961). Also, S1P promotes the migration of bone marrow-derived EC precursors to neovascularization sites (Annabi, Exp Hematol. 2003 July; 31(7):640-9.). Cells that over-express $S1P_1$ are resistant to the anti-angiogenic agents thalidomide and Neovastat (Annabi, Exp Hematol. 2003 July; 31(7):640-9.). In addition, it has been demonstrated that substantial cross-talk exists between S1P and other pro-angiogenic growth factors such as VEGF, EGF, PDGF, bFGF and IL-8. For example, S1P transactivates EGF (Shida, et al., 2004) and VEGF2 receptors (Spiegel & Milstien, 2003), and VEGF up-regulates $S1P_1$ receptor expression (Igarashi, et al., 2003). Also, S1P, acting via $S1P_1$ and the "VEGF axis" is required for hind-limb angiogenesis and neovascularization (Chae, et al., 2004). Anti-angiogenic drug, monoclonal anti-VEGF antibody bevacizumab (Avastin, Genentech) has been approved for treatment of colon cancer in combination with chemotherapy. S1P has also been shown to be involved in metastasis [Takuwa, Biochim Biophys Acta 2002, 1582: 112-120].

Functional S1P receptor antagonist FTY720 inhibited tumor growth and tumor-associated angiogenesis in models of hepatocellular carcinoma, blast crisis chronic myelogenous leukemia, Philadelphia chromosome-positive acute lymphocytic leukemia, chronic lymphocytic leukemia, lymphoblastic leukemia/lymphoma, and lung tumors [Ho, Mol Cancer Ther 2005, 4: 1430-1438; Neviani, J Clin Invest 2007, 117: 2408-2421; Liu, Blood 2008, 111: 275-284; Lucas da Silva, J Exp Ther Oncol 2008, 7: 9-15]. Although these studies strongly suggest that the majority of tumor-promoting functions of S1P are mediated by its cell surface receptors, it should be considered that that S1P may as well act as an intracellular second messenger [Hait, Science 2009, 325: 1254-1257; Alvarez, Nature 2010, 465: 1084-1088]. S1P has for example been identified as a direct intracellular ligand of histone deacetylases, which are as well implicated in the development and progression of cancer [Hait, Science 2009, 325: 1254-1257].

A neutralizing anti-S1P antibody significantly blocked tumor growth and tumor-associated angiogenesis. The antibody inhibited bFGF- and VEGF-induced angiogenesis in a murine Matrigel plug assay, and the antibody inhibited the release of proangiogenic growth factors (VEGF, IL-8, IL-6) from tumor cells in vitro and in vivo. It inhibited tumor progression in mouse models of breast carcinoma, ovarian cancer, in a lung adenocarcinoma xenograft model and in an allograft model of murine melanoma [Visentin, Cancer Cell. 2006 March; 9(3):225-38]. Hyperplasia is referred to as a hyperproliferation of cells in a normal tissue or organ. A clinically relevant example is bengin prostate hyperplasia. The hyperproliferative effect of S1P has been associated with hyperplasia. Phenoxodiol which results in a decrease of S1P content has been tested in different types of cancer and prostate cancer [Marshall Edwards press release Jun. 1, 2010].

Altogether, there is compelling evidence for the contribution of S1P to hyperproliferation, angiogenesis and metastasis. Irrespective of the contributions of the individual processes to pathogenesis, direct targeting of S1P by neutralizing agents, such as a S1P binding nucleic acid molecule is expected to provide an effective treatment for diseases characterised by excessive proliferation, angiogenesis, metastasis, and resistance to apoptosis, such as most types of tumors and cancers.

S1P regulates motility, adhesion and trafficking of lymphocytes. S1P regulates the exit of lymphocytes from lymphoid organs and their retention at the site of inflammation [Matloubian, Nature 2004, 427, 355-360; Ledgerwood, Nat. Immunol. 2008, 9, 42-53]. Reduction of plasma S1P levels results in lymphopenia, thus, directing pathogenic T lymphocytes away from inflammation sites thereby being useful in the treatment of inflammatory diseases [Schwab, Science 2005, 309(5741):1735-9; Japtok and Kleuser, Curr Opin Investig Drugs. 2009 November; 10(11):1183-94]. Furthermore S1P has been shown to induce the production of proinflammatory factors such as prostaglandins, TNF-alpha and IL-6 [Lai, J Immunol 2008, 181: 8010-17; Lai, J Immunol 2009, 183: 2097-2103].

FTY720 is phosphorylated in vivo and serves as an agonist for all S1P receptors 1, 3, 4, and 5). Activation of S1P receptors by FTY720 in turn results in a down-regulation of receptor availability at the cell surface. This renders cells unresponsive to S1P and blocks the egress of lymphocytes from lymphoid tissues resulting in an immunosuppressive effect of FTY720 [Mandala, Science 2002, 296: 346-349; Gräler, Faseb J 2004, 18: 551-553]. FTY720 showed efficacy in various autoimmune models and is approved for the treatment of multiple sclerosis.

S1P and S1P1 receptor expression is reported to be upregulated in synovial lining cells, vascular endothelial cells, and inflammatory mononuclear cells in synovium rheumatoid arthritis compared to osteoarthritis patients [Kitano, Arthritis Rheum. 2006 March; 54(3):742-53; Lai, J. Immunol. 2008 Dec. 1; 181(11):8010-7]. In the collagen-induced arthritis model a sphingosine kinase inhibitor significantly inhibited disease severity and reduced articular inflammation and joint destruction [Lai, J. Immunol. 2008 Dec. 1; 181(11):8010-7]. In agreement, functional S1P receptor antagonist FTY720 inhibited bone destruction in the SKG mouse model of rheumatoid arthritis [Tsunemi, Clin Immunol. 2010 August; 136 (2):197-204].

Due to the immunosuppressive effect of S1P receptor functional antagonist FTY720 it is suggested that reducing the effective in vivo concentration of S1P with neutralizing agents, such as S1P-binding nucleic acid molecules, will be beneficial for the treatment of inflammatory skin diseases, such as lupus erythematosus, psoriasis, and atopic dermatitis [Herzinger, Am J Clin Dermatol. 2007; 8(6):329-36].

Systemic administration of S1P has been shown to increase bronchial hyperresponsiveness in mice [Roviezzo, Am J Respir Cell Mol. Biol. 2010 May; 42(5): 572-7]. Local application of functional S1P receptor antagonist FTY720 via inhalation suppressed allergic airway inflammation murine models of asthma [Idzko, J Clin Invest 2006, 116: 2935-2944; Nishiuma, Am J Physiol Lung Cell Mol. Physiol. 2008 June; 294(6):L1085-93].

SPH kinase-deficient mice developed a significantly ameliorated disease in a model of inflammatory bowel disease (IBD) [Snider, FASEB J. 2009 January; 23(1):143-52]. In agreement, functional S1P receptor antagonist FTY720 efficiently inhibited disease development in a mouse IBD model [Deguchi, Oncol Rep. 2006 October; 16(4):699-703].

At low doses functional S1P receptor antagonist FTY720 has been shown to enhance endothelial barrier function and reduce lung permeability in a mouse model of ventilator-induced lung injury (VILI) (Müller, Pulm Pharmacol Ther. 2011 Mar. 23, Epub ahead of print). Thus, reducing effective pulmonary S1P concentrations may suppress inflammation and enhance pulmonary endothelial barrier function in different clinically relevant situations, such a pneumonia, chronic obstructive pulmonary disease (COPD) or pulmonary arterial hypertension (PAH). There is further evidence that inhibition of sphingosine kinase, and thereby a reduction of effective S1P levels, might ameliorate lung injury after trauma and hemorrhagic shock [Lee, J. Trauma. 2004, 57(5): 955-60].

Bacterial products increase SphK1 expression and function in human phagocytes in vitro, as well as in sepsis patients. Blockade of SphK1 inhibited LPS-induced cytokine production in human phagocytes and increased survival of septic mice. Importantly, the therapeutic effects of antibiotic treatment on survival in sepsis were enhanced by SphK1 blockade [Puneet, Science, 2010 Jun. 4; 328(5983):1290-4].

In animal models of organ transplantation S1P 1 antagonists prolonged skin and heart allograft survival and attenuated chronic rejection [Shimizu, Circulation 2005, 111, 222-229]. Similarly, functional S1P receptor antagonist FTY720 significantly prolonged graft survival in orthotopic mouse models of corneal transplantation and in a rat-to-mouse model of corneal xenotransplantation [Zhang, et al. (2003), Transplantation, vol 76: 1511-3; Sedlakova, et al. (2005), Transplantation, vol 79, 297-303].

In an adoptive transfer mouse model of type 1 diabetes the functional S1P antagonist fingolimod slowed disease progression [Morris, Autoimmunity. 2011 March; 44(2):115-28].

Treatment with fingolimod significantly reduced inflammatory infiltration and tissue disruption in a model of inflammatory prostatitis [Zhang, Scand J. Immunol. 2011 Feb. 15].

Treatment with functional S1P receptor antagonist FTY720 significantly reduced proteinuria and tubuli injury in streptozotocin-treated rats. This indicates that inhibition of S1P by a neutralizing agent, such as a S1P binding nucleic acid molecule, could be beneficial in diabetic nephropathy.

Inhibition of sphingosine kinase-2 has been reported to attenuate the knee joint histological damage and pain associated with monosodium iodoacetate-induced osteoarthritis in rats [Fitzpatrick, Pharmacology. 2011; 87(3-4):135-43].

S1P2 receptor signalling has been implicated in the pathogenesis of atherosclerosis[Skoura, Arterioscler Thromb Vasc Biol. 2011 January; 31(1):81-5].

Mice over-expressing SPHK1 show a profound cardiac remodelling associated with myocardial fibrosis [Takuwa, Cardiovasc Res 2009, 85: 484-493]. Neutralizing anti-S1P antibody inhibits collagen production by primary cardiac fibroblasts [Gellings Lowe, Cardiovasc Res 2009, 82: 303-312].

Accordingly, disease and/or disorders and/or diseased conditions for the treatment and/or prevention of which the medicament according to the present invention may be used include, but are not limited to a) ocular diseases, preferably such ocular disease is selected from the group comprising age-related macular degeneration, diabetic retinopathy with diabetic macular edema, retinal pigmented epithelium detachment in either age-related macular degeneration or diabetic retinopathy, proliferative vitreoretinopathy and retinal fibrosis in age-related macular degenerationor diabetic retinopathy, b) cancer, preferably such cancer is selected from the group comprising breast cancer, ovarian cancer, melanoma, lung cancer, hyperplasia such as prostate hyperplasia, c) inflammatory disease, wherein preferably such inflammatory disease is selected from the group comprising autoimmune disease, multiple sclerosis, rheumatoid arthritis, psoriasis, asthma, inflammatory bowel disease, pneumonia, sepsis and trauma such as ventilator-induced lung injury and sepsis, wherein preferably the autoimmune disease is selected from the group comprising multiple sclerosis, rheumatoid arthritis, psoriasis, asthma and inflammatory bowel disease.

In a further embodiment, the medicament comprises a further pharmaceutically active compound.

Alternatively, or additionally, such further pharmaceutically active compound is a further nucleic acid according to the present invention. Alternatively, the medicament comprises at least one more nucleic acid which binds to a target molecule different from S1P or exhibits a function which is different from the one of the nucleic acids according to the present invention. Preferably such at least one more nucleic acid exhibits a function similar or identical to the one of one or several of the further pharmaceutically active compound(s) disclosed herein.

It is within the present invention that the medicament is alternatively or additionally used, in principle, for the prevention of any of the disease disclosed in connection with the use of the medicament for the treatment of said diseases. Respective markers therefore, i.e. for the respective diseases are known to the ones skilled in the art. Preferably, the respective marker is S1P.

In one embodiment of the medicament of the present invention, such medicament is for use in combination with other treatments for any of the diseases disclosed herein, particularly those for which the medicament of the present invention is to be used.

A composition according to the invention can also be administered in combination with another therapeutic agent or therapeutic regimen. In addition, the modulation of S1P through a neutralizing agent may be useful in inducing a temporary modulation of vascular permeability to allow or enhance treatment with a second therapeutic reagent whose effect may be increased or improved through such a combinatorial treatment.

The medicament according to the present invention may be used for the treatment and/or prevention of cancer in combination with a second medicament or a second pharmaceutically active agent, whereby the second medicament or the second pharmaceutically active agent damages, destroys and/or labels (the) cancer cells. Such second medicament or second pharmaceutically active agent are preferably selected from but not restricted to the group comprising
a) antibodies such as Rituximab (target CD20), Cetuximab (target epidermal growth factor receptor), Ibritumomab-Tiuxetan (target CD20), Tositumomab (target CD20), Trastuzumab (target HER2/neu), Bevacizumab (target VEGF);
b) alkylating agents such as cisplatin, carboplatin, oxaliplatin, mechlorethamine, cyclophosphamide, chlorambucil, Doxorubicin, Melphalan;
c) anti-metabolites such as purineazathioprine, mercaptopurine, Fludarabine;
d) plant alkaloids such vinca alkaloids, plant terpenoids such as taxanes, preferably Docetaxel, Paclitaxel, podophyllotoxin, epothilone;
e) topoisomerase inhibitors such as camptothecins, Irinitecan;
f) and other such as Leucovorin, Methotrexate, Tamoxifen, Sorafenib, Lenalidomide, Bortezomib, Dexamethasone, Fluorouracil.

The medicament according to the present invention may be used for the treatment and/or prevention of an ocular disease in combination with a second medicament or a second pharmaceutically active agent, whereby the second medicament or the second pharmaceutically active agent is preferably selected from but not restricted to the group comprising
a) those known to suppress the immune system such as calcineurin inhibitors, cyclosporins, methotrexate, azathioprin, tacrolimus, rapamycin, chlorambucil, leflunomide, mycophenolate mofetil, brequinar, mizoribin, thalidomide, or deoxyspergualin; corticosteroids like prednisone, methylprednisolone, hydrocortisone, dexamethasone, triamcinolone, betamethasone, effervescent, or budesonide.
b) anti-inflammatory or anti-angiogenic biologics can be used in combination such as IL-10, erlizumab, tolermab, rituximab, gomiliximab, basiliximab, daclizumab, HuMax-TAC, visilizumab, HuMaxCD4, clenoliximab, MAX 16H5, TNX 100, toralizumab, alemtuzumab, CY 1788, galiximab, pexelizumab, eculizumab, PMX-53, ETI 104, FG 3019, bertilimumab, 249417 (anti-factor IX) abciximab, YM 337, omalizumab, talizumab, fontolizumab, J695 (anti-IL12), HuMaxIL-15, mepolizumab, elsilimomab, HuDREG, anakinra, Xoma-052, adalimumab, infliximab, certolizumab, afelimomab, CytoFab, AME 527, Vapaliximab, bevacizumab, ranibizumab, vitaxin, belimumab, MLN 1202, volociximab, F200 (anti-α5β1), efalizumab, m60.11 (anti.CD11b), etanercept, onercept, natalizumab, or siplizumab, tocilizumab, ustekinumab, ABT-874., VEGF-trap eye.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, preferably by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiancy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

Effective plasma levels of the nucleic acid according to the present invention preferably range from 500 fM to 200 µM, preferably from 1 nM to 20 µM, more preferably from 5 nM to 20 µM, most preferably 50 nM to 20 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is need of such treatment, whereby the method comprises the administration of a pharmaceutically effective amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of S1P in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagostic agent or diagnostic means is suitable to detect, either directly or indirectly S1P, preferably S1P as described herein and more preferably S1P as described herein in connection with the various disorders and diseases described herein. The diagnostic is suitable for the detection and/or follow-up of any of the disorders and diseases, respectively, described herein. Such detection is possible through the binding of the nucleic acids according to the present invention to S1P. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to S1P. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like an secondary antibody).

In a further embodiment the nucleic acid molecules according to the invention are detected or analysed by a second detection means, wherein the said detection means is a molecular beacon. The methodology of molecular beacon is known to persons skilled in the art and reviewed by Mairal et al. (Mairal et al., 2008, Anal Bioanl Chem 390(4), 989-1007).

It will be acknowledged that the detection of S1P using the nucleic acids according to the present invention will particularly allow the detection of S1P as defined herein.

In connection with the detection of S1P a preferred method comprises the following steps:
  (a) providing a sample which is to be tested for the presence of S1P,
  (b) providing a nucleic acid according to the present invention,
  (c) reacting the sample with the nucleic acid, preferably in a reaction vessel whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of S1P and the nucleic acid, whereby more preferably said complex is detected. It is within an embodiment that from the complex the S1P is detected.

A respective detection means which is in compliance with this requirement is, for example, any detection means which is specific for that/those part(s) of the S1P. A particularly preferred detection means is a detection means which is selected from the group comprising nucleic acids, polypeptides, proteins and antibodies, the generation of which is known to the ones skilled in the art.

The method for the detection of S1P also comprises that the sample is removed from the reaction vessel which has preferably been used to perform step c).

The method comprises in a further embodiment also the step of immobilising an interaction partner of S1P on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radiolabel, and a chelator molecule. Alternatively, the second detection means interacts with the detection label which is preferably contained by, comprised by or attached to the nucleic acid. Particularly preferred combinations are as follows:

- the detection label is biotin and the second detection means is an antibody directed against biotin, or wherein
- the detection label is biotin and the second detection means is an avidin or an avidin carrying molecule, or wherein
- the detection label is biotin and the second detection means is a streptavidin or a stretavidin carrying molecule, or wherein
- the detection label is biotin and the second detection means is a neutravidin or a neutravidin carrying molecule, or
- wherein the detection label is a bromo-desoxyuridine and the second detection means is an antibody directed against bromo-desoxyuridine, or wherein
- the detection label is a digoxigenin and the second detection means is an antibody directed against digoxigenin, or wherein
- the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of S1P being immobilised on a surface and the nucleic acid according to the present invention is preferably added to the complex formed between the interaction partner and the S1P, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and S1P and free S1P.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the S1P is detected using fluorescence.

In an embodiment of the method a signal is created in step (c) or step (d) and preferably the signal is correlated with the concentration of S1P in the sample.

In a preferred aspect, the assays may be performed in 96-well plates, where components are immobilized in the reaction vessels as described above and the wells acting as reaction vessels.

The inventive nucleic acid may further be used as starting material for drug discovery. Basically, there are two possible approaches. One approach is the screening of compound libraries whereas such compound libraries are preferably low molecular weight compound libraries. In an embodiment the screening is a high throughput screening. Preferably, high throughput screening is the fast, efficient, trial-and-error evaluation of compounds in a target based assay. In best case the analysis are carried by a colorimetric measurement. Libraries as used in connection therewith are known to the one skilled in the art.

In case of screening of compound libraries, such as by using a competitive assay which are known to the one skilled in the arts, appropriate S1P analogues, S1P agonists or S1P antagonists may be found. Such competitive assays may be set up as follows. The inventive nucleic acid, preferably a spiegelmer which is a target binding L-nucleic acid, is coupled to a solid phase. In order to identify S1P analogues labelled S1P may be added to the assay. A potential analogue would compete with the S1P molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids, preferably for the detection of a lipid, more preferably for the detection of S1P. Additionally, the kit may comprise at least one or several positive or negative controls. A positive control may, for example, be S1P, particularly the one against which the inventive nucleic acid is selected or to which it binds, preferably, in liquid form. A negative control may, e.g., be a peptide which is defined in terms of biophysical properties similar to S1P, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of the nucleic acid according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. The capture probe is immobilised to a surface or matrix. The detection probe preferably carries a marker molecule or label that can be detected as previously described herein.

The detection of the nucleic acid according to the present invention can be carried out as follows: The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ.ID. Nos., the chemical nature of the nucleic acid molecules according to the present invention and the target molecules S1P as used herein, the actual sequence thereof and the internal reference number is summarized in the following table.

| SEQ. ID. No. | sub-stance | Structure/Sequence | Internal Reference |
|---|---|---|---|
| 1 | D-RNA | AGCGUGAAUAGCCGUUGAAACGCCUUUAGAGAAGCACUAGCACGCU | 215-F9-001, S1P-215-F9-001 |
| 2 | D-RNA | AGCGUGAAUAGCCGAUGAAACGCCUUUAGAGAAGCACUAGCACGCU | 215-H11-001 |
| 3 | D-RNA | AGCGUGAAUAGCCGAAUGAAACGCCUUUAGAGAAGCACUAGCACGCU | 215-H9-001 |
| 4 | D-RNA | AGCGUGAAUAGCCGAAUGAAACGCCUUAAGAGAAGCACUAGCACGCU | 215-F10-001 |
| 5 | D-RNA | GCGUGUAUAGCCGUUGAAACGCCUUUAGAGAAGCACUAGCACGC | 222-A10-002 |
| 6 | D-RNA | GCGUGAAUAGCCGAAUGAAACGCCUUUAGAGAAGCACUAGCACGC | 222-A12-002 |
| 7 | D-RNA | GCGUGAAUAGCCGUUGAAACGCCUUUAGAGAAGCACUAGCACGC | 215-F9-002 |
| 8 | D-RNA | CGUGAAUAGCCGUUGAAACGCCUUUAGAGAAGCACUAGCACG | 215-F9-003 |
| 9 | D-RNA | GUGAAUAGCCGUUGAAACGCCUUUAGAGAAGCACUAGCAC | 215-F9-004 |
| 10 | D-RNA | GCUGAAUAGCCGUUGAAACGCCUUUAGAGAAGCACUAGCAGC | 215-F9-008 |
| 11 | D-RNA | GGUGAAUAGCCGUUGAAACGCCUUUAGAGAAGCACUAGCACC | 215-F9-009 |
| 12 | L-RNA | AGCGUGAAUAGCCGUUGAAACGCCUUUAGAGAAGCACUAGCACGCU | 215-F9-001, L-S1P-215-F9-001 |
| 13 | L-RNA | AGCGUGAAUAGCCGAUGAAACGCCUUUAGAGAAGCACUAGCACGCU | 215-H11-001 |
| 14 | L-RNA | AGCGUGAAUAGCCGAAUGAAACGCCUUUAGAGAAGCACUAGCACGCU | 215-H9-001 |
| 15 | L-RNA | AGCGUGAAUAGCCGAAUGAAACGCCUUAAGAGAAGCACUAGCACGCU | 215-F10-001 |
| 16 | L-RNA | GCGUGUAUAGCCGUUGAAACGCCUUUAGAGAAGCACUAGCACGC | 222-A10-002 |
| 17 | L-RNA | GCGUGAAUAGCCGAAUGAAACGCCUUUAGAGAAGCACUAGCACGC | 222-A12-002 |
| 18 | L-RNA | GCGUGAAUAGCCGUUGAAACGCCUUUAGAGAAGCACUAGCACGC | 215-F9-002, L-S1P-215-F9-002 |
| 19 | L-RNA | CGUGAAUAGCCGUUGAAACGCCUUUAGAGAAGCACUAGCACG | 215-F9-003 |
| 20 | L-RNA | GUGAAUAGCCGUUGAAACGCCUUUAGAGAAGCACUAGCAC | 215-F9-004 |
| 21 | L-RNA | GCUGAAUAGCCGUUGAAACGCCUUUAGAGAAGCACUAGCAGC | 215-F9-008 |
| 22 | L-RNA | GGUGAAUAGCCGUUGAAACGCCUUUAGAGAAGCACUAGCACC | 215-F9-009 |
| 23 | L-RNA | 5'-PEG-AGCGUGAAUAGCCGUUGAAACGCCUUUAGAGAAGCACUAGCACGCU | 215-F9-001-5'-PEG; NOX-S92 |
| 24 | L-RNA | 5'-PEG-GCGUGAAUAGCCGUUGAAACGCCUUUAGAGAAGCACUAGCACGC | 215-F9-002-5'-PEG, 5'-40 kDa-PEG-L-S1P-215-F9-002, NOX-S91 |
| 25 | L-RNA | 5'-NH$_2$-AGCGUGAAUAGCCGUUGAAACGCCUUUAGAGAAGCACUAGCACGCU | 215-F9-001-5'-Amino |

-continued

| SEQ. ID. No. | sub-stance | Structure/Sequence | Internal Reference |
|---|---|---|---|
| 26 | L-RNA | 5'-NH₂-GCGUGAAUAGCCGUUGAAACGCCUUUAGAGAAGCACUAGCACGC | 215-F9-002-5'-Amino |
| 27 | L-RNA/ L-DNA | dGCGUGAAUAGCCGUUGAAACGCCUUUAGAGAAGCACUAGCACGC | L-S1P-215-F9-002-D01 |
| 28 | L-RNA/ L-DNA | GCGUGAAUAGdCCGUUGAAACGCCUUUAGAGAAGCACUAGCACGC | L-S1P-215-F9-002-D11 |
| 29 | L-RNA/ L-DNA | GCGUGAAUAGCCGUUGAAdACGCCUUUAGAGAAGCACUAGCACGC | L-S1P-215-F9-002-D19 |
| 30 | L-RNA/ L-DNA | GCGUGAAUAGCCGUUGAAACdGCCUUUAGAGAAGCACUAGCACGC | L-S1P-215-F9-002-D21 |
| 31 | L-RNA/ L-DNA | GCGUGAAUAGCCGUUGAAACGdCCUUUAGAGAAGCACUAGCACGC | L-S1P-215-F9-002-D22 |
| 32 | L-RNA/ L-DNA | GCGUGAAUAGCCGUUGAAACGCCUUUAGAGAdAGCACUAGCACGC | L-S1P-215-F9-002-D32 |
| 33 | L-RNA/ L-DNA | GCGUGAAUAGCCGUUGAAACdGdCCUUUAGAGAAGCACUAGCACGC | L-S1P-215-F9-002-D21-22 |
| 34 | L-RNA/ L-DNA | GCGUGAAUAGCCGUUGAAdAC dGCCUUUAGAGAAGCACUAGCACGC | L-S1P-215-F9-002-D21-19 |
| 35 | L-RNA/ L-DNA | GCGUGAAUAGCCGUUGAAdACdGdCCUUUAGAGAAGCACUAGCACGC | L-S1P-215-F9-002-D21-19-22 |
| 36 | L-RNA/ L-DNA | dGCGUGAAUAGCCGUUGAAdACdGCCUUUAGAGAdAGCACUAGCACGC | L-S1P-215-F9-002-D01-19-21-32 |
| 37 | L-RNA/ L-DNA | dGCGUGAAUAGdCCGUUGAAdACdGCCUUUAGAGAdAGCACUAGCACGC | L-S1P-215-F9-002-D01-11-19-21-32 |
| 38 | D-RNA/ L-RNA | GG-GCGUGAAUAGCCGUUGAAACGCCUUUAGAGAAGCACUAGCACGC 5'-GG is D-RNA | L-S1P-215-F9-002-5'diD-G |
| 39 | L-RNA/ L-DNA | 5'-NH2dGCGUGAAUAGCCGUUGAAdACdGCCUUUAGAGAdAGCACUAGCACGC | L-S1P-215-F9-002-D01-19-21-32-5'-Amino |
| 40 | L-RNA/ L-DNA | 5'-PEGdGCGUGAAUAGCCGUUGAAdACdGCCUUUAGAGAdAGCACUAGCACGC | 5'-40 kDa-PEG-L-S1P-215-F9-002-D01-19-21-32, S1P-215-F9-002-D01-19-21-32-5'-PEG, NOX-S93 |
| 41 | L-RNA | WAUUGCCGAWUGUAACGCCUUWAGAGAAAGCACUAG | Consensus sequence I |
| 42 | L-RNA | WAUUGCCGWUGUAACGCCUUWAGAGAAAGCACUAG | Consensus sequence II |

The present invention is further illustrated by the figures, examples and the sequence listing from which further features, embodiments and advantages may be taken, wherein FIG. 1 shows an alignment of sequences of S1P binding nucleic acids;

FIG. 2 shows the minimal binding sequence of the S1P binding nucleic acid 215-F9-001 and its derivatives;

FIG. 6 show derivatives of S1P binding spiegelmer 215-F9-002 (also referred to as L-S1P-215-F9-002) consisting of ribonucleotide(s) (A, U, G, C) and at least one 2'-deoxyribonucleotide(s) (dA, dT, dG, dC);

Figure 7:
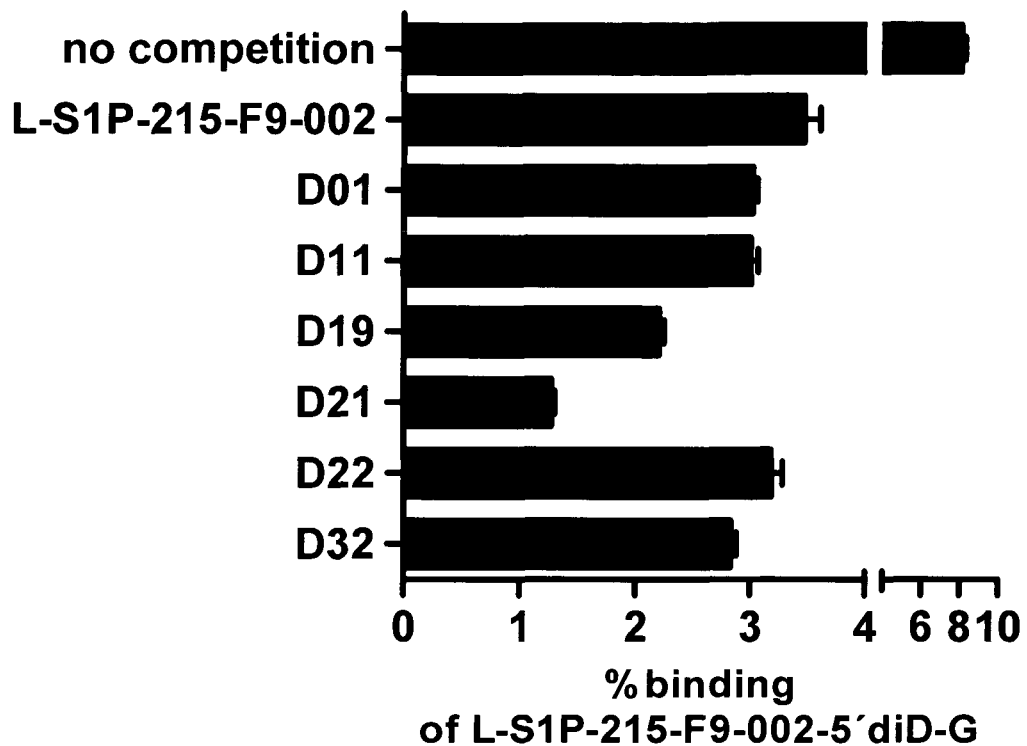

FIG. 7 shows the results of the competitive spiegelmer pull-down assays carried out with derivatives of S1P binding spiegelmer 215-F9-002 (also referred to as L-S1P-215-F9-002) consisting of ribonucleotide(s) (A, U, G, C) and at least one 2'-deoxyribonucleotide(s) (dA, dT, dG, dC): 0.3 nM radioactively labeled L-S1P-215-F9-002-5'diD-G binding to 8 nM biotinylated D-e-S1P at 37° C. competed by 50 nM unlabeled spiegelmer (triplicates) as indicated;

FIG. 8 shows the results of the competitive spiegelmer pull-down assays derivatives of S1P binding spiegelmer 215-

F9-002 (also referred to as L-S1P-215-F9-002) consisting of ribonucleotide(s) (A, U, G, C) and at least one 2'-deoxyribonucleotide(s) (dA, dT, dG, dC), whereby
- (A) 0.3 nM radioactively labeled L-S1P-215-F9-002-5'diD-G binding to 8 nM biotinylated D-e-S-1-P for 3 h at 37° C. competed by 36 nM unlabeled Spiegelmer (triplicates) as indicated;
- (B) 0.5 nM radioactively labeled L-S1P-215-F9-002-5'diD-G binding to 7 nM biotinylated D-e-S-1-P for 2.5 h at 37° C. competed by titrating concentrations of 5'-40 kDa-PEG-L-S1P-215-F9-002 (also referred to as NOX-S91, circles;) and 5'-40 kDa-PEG-L-S1P-215-F9-002-D01-19-21-32 (also referred to as NOX-S93; squares)

FIG. 9 shows the results of the inhibition of (Mean values of triplicate cultures±SD are shown):
- 10 nM D-e-S1P-induced β-arrestin recruitment in a reporter cell line expressing EDG1 by:
  - (A) 5'-40 kDa-PEG-L-S1P-215-F9-002 (also referred to as NOX-S91) and
  - (B) 5'-40 kDa-PEG-L-S1P-215-F9-002-D01-19-21-32 also referred to as NOX-S93)
- Inhibition of 10 nM D-e-S1P-induced calcium release in a cell line expressing EDG3 by:
  - (C) 5'-40 kDa-PEG-L-S1P-215-F9-002 8 also referred to as NOX-S91) and
  - (D) 5'-40 kDa-PEG-L-S1P-215-F9-002-D01-19-21-32 (also referred to as NOX-S93);

FIG. 10 shows the effects of spiegelmers NOX-S91 and NOX-S93 in a spheroid-based cellular angiogenesis in vitro assay, whereby the spiegelmers were tested for their ability to inhibit VEGF-A (Vascular Endothelial Growth Factor-A) and S1P (sphingosine-1-phosphate) induced sprouting of human umbilical vein endothelial cells (HUVEC).

EXAMPLE 1

Nucleic Acids that Bind Sphingosine 1-phosphate (S1P)

Using biotinylated L-e-S1P as a target, several S1P binding nucleic acids and derivatives thereof could be generated: the nucleotide sequences of which are depicted in FIGS. 1, 2 and 6. The nucleic acids were characterized as
- a) aptamers, i.e. as D-nucleic acid using a direct pull-down assay (Example 3) and/or a competitive pull-down assay (Example 3)
- b) spiegelmers, i.e. L-nucleic acid using a competitive pull-down assay (Example 6), an in vitro assay with the S1P receptor EDG-3/S1P$_3$ or EDG-1/S1P$_1$(Example 4). Moreover spiegelmers were tested in an in vitro angiogenesis assay (Example 7) and in vivo (Example 5). The spiegelmers and aptamers were synthesized as described in Example 2.

The nucleic acid molecules thus generated exhibit slightly different sequences, whereby one main type was identified and defined as S1P binding nucleic acids, and are depicted in FIGS. 1, 2 and 6.

For definition of nucleotide sequence motifs, the IUPAC abbreviations for ambiguous nucleotides are used:

| S | strong | G or C; |
|---|---|---|
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

1.1 S1P Binding Nucleic Acids

As depicted in FIG. 1 and FIG. 2 the S1P binding nucleic acids comprise one central stretch of nucleotides defining a potential S1P binding motif.

In general, S1P binding nucleic acids comprise at their 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule.

The three stretches of nucleotides of S1P binding nucleic acids—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. However, alternatively, the first terminal stretch of nucleotides, the central stretch of nucleotides and the terminal second stretch of nucleotides are arranged to each other in 5'→3'-direction: the second terminal stretch of nucleotides—the central stretch of nucleotides—the first terminal stretch of nucleotides.

The sequences of the defined box or stretches may be different between the S1P binding nucleic acids which influences the binding affinity to S1P. Based on binding analysis of the different S1P binding nucleic acids the central stretch and their nucleotide sequences as described in the following are individually and more preferably in their entirety essential for binding to human S1P.

Figure 3:
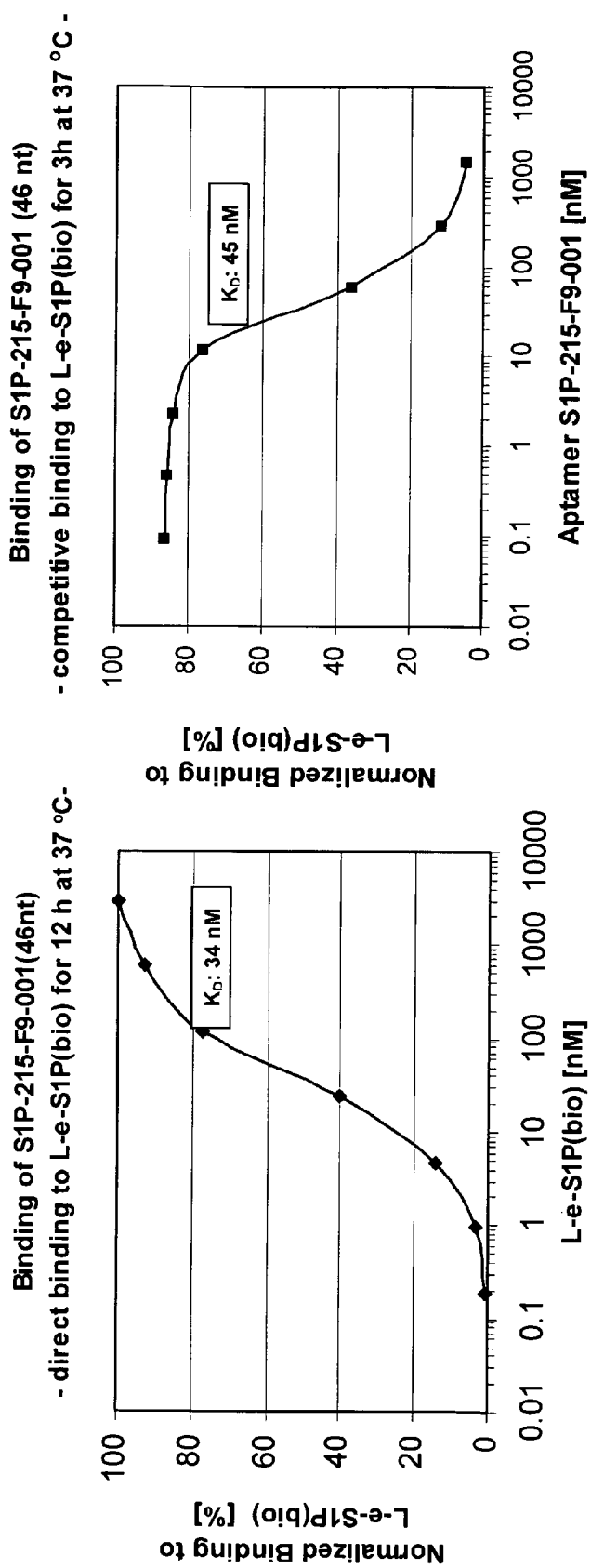
FIG. 3 shows analysis of S1P binding aptamer 215-F9-001 (also referred to as S1P-215-F9-001) by a direct and a competitive pull-down assay.

The S1P binding nucleic acids according to the present invention are shown in FIGS. 1 and 2. All of them were tested as aptamers for their ability to bind S1P, more precisely biotinylated L-e-S1P (also referred to as L-e-S1P(bio)). The first S1P binding nucleic acid that was characterized for its binding affinity to S1P is nucleic acid 215-F9-001. The equilibrium binding constant $K_D$ was determined by direct and competitive pull-down binding assays ($K_{Ddirect}$=34 nM, $K_{Dcomp.}$=45 nM; FIGS. 1 and 3).

The S1P binding nucleic acids 215-H11-001, 215-H9-001, 215-F10-001, 222-A10-002 and 222-A12-002 were tested as aptamers in comparative competition pull-down assays vs. S1P binding nucleic acid 215-F9-001. S1P binding nucleic acids 215-F10-001 and 215-H11-001 showed similar binding affinity as 215-F9-001 (FIG. 1). The S1P binding nucleic acids 215-H9-001, 222-A10-002 and 222-A12-002 showed reduced binding affinity in comparison to S1P binding nucleic acid 215-F9-001 (FIG. 1).

The derivatives 215-F9-002 and 215-F9-003 of S1P binding nucleic acid 215-F9-001 showed similar binding to S1P as 215-F9-001 whereas the derivatives 215-F9-004, 215-F9-008 and 215-F9-009 showed reduced binding affinity in a competitive pull-down assay in comparison to S1P binding nucleic acid 215-F9-001 (FIG. 2).

The S1P binding nucleic acids according to the present invention comprise a central stretch of nucleotides with a length of 34 or 35 nt.

The S1P binding nucleic acids according to the present invention share the sequence 5' WAUUGCCGAWU-GUAACGCCUUWAGAGAAAGCACUAG 3' (SEQ ID NO: 41) or 5' WAUUGCCGWUGUAACGCCUUWA-GAGAAAGCACUAG 3' (SEQ ID NO: 42) for the central stretch of nucleotides. The S1P binding nucleic acids 215-F9-001, 215-H11-001, 215-F10-001 and the derivates of 215-F9-001 that showed the best binding affinity to S1P comprise the following sequences for the central stretch:

a) 215-F9-001 and derivatives:    (SEQ ID NO: 43)
AAUAGCCGUUGAAACGCCUUUAGAGAAGCACUAG b) 215-H11-001:                   (SEQ ID NO: 44)
AAUAGCCGAUGAAACGCCUUUAGAGAAGCACUAG c) 215-F10-001:                   (SEQ ID NO: 45)
AAUAGCCGAAUGAAACGCCUUAAGAGAAGCACUAG.

The 5'- and 3-terminal stretches of S1P bindig nucleic acids comprise three (e.g. 215-F9-004), four (e.g. 215-F9-003), five (e.g. 215-F9-002) or six (e.g. 215-F10-001) nucleotides (FIG. 1 and FIG. 2), whereby the stretches optionally hybridize with each other, whereby upon hybridization a double-stranded structure is formed. This double-stranded structure can consist of three to six basepairs. However, such hybridization is not necessarily given in the molecule.

Combining the first terminal stretches of nucleotides and the second terminal stretches of nucleotides of all tested S1P binding nucleic acids the generic formula are of 5' $X_1X_2X_3SUG$ 3' (first terminal stretch of nucleotides) and 5' $CASX_4X_5X_6$ 3' (second stretch of nucleotides), wherein $X_1$ is A or absent, $X_2$ is G or absent, $X_3$ is S or absent, $X_4$ is S or absent, $X_5$ is C or absent, and $X_6$ is U or absent.

The S1P binding sequence 215-F9-004 with three nucleotide long terminal stretches and the identical central stretch as S1P binding sequence 215-F9-001 showed decreased binding affinity in comparison to S1P binding sequence 215-F9-001 with six nucleotide long terminal stretches (FIG. 2). Therefore the preferred length of the terminal stretches of S1P binding nucleic acids according to the present invention is 4-6 nucleotides.

Combining the first terminal stretches of nucleotides and the second terminal stretches of nucleotides of S1P binding nucleic acids with five to six nucleotides the generic formula are of 5' $X_1X_2X_3SUG$ 3' (first terminal stretch of nucleotides) and 5' $CASX_4X_5X_6$ 3' (second stretch of nucleotides), wherein
a) $X_1$ is A, $X_2$ is G, $X_3$ is S, $X_4$ is S, $X_5$ is C, and $X_6$ is U or
b) $X_1$ is absent, $X_2$ is G, $X_3$ is S, $X_4$ is S, $X_5$ is C, and $X_6$ is U or
c) $X_1$ is A, $X_2$ is G, $X_3$ is S, $X_4$ is S, $X_5$ is C, and $X_6$ is absent or
d) $X_1$ is absent, $X_2$ is G, $X_3$ is S, $X_4$ is S, $X_5$ is C, and $X_6$ is absent,
wherein preferably
a) the first terminal stretch of nucleotides comprises a nucleotide sequence of 5' AGCGUG 3' and the second terminal stretch of nucleotides comprises a nucleotide sequence of 5' CACGCU 3' (see e.g. 215-F9-001) or
b) the first terminal stretch of nucleotides comprises a nucleotide sequence of 5' GCGUG 3' and the second terminal stretch of nucleotides comprises a nucleotide sequence of 5' CACGC 3 (see e.g. 215-F9-002)'.

Combining the first terminal stretches of nucleotides and the second terminal stretches of nucleotides of S1P binding nucleic acids with four to five nucleotides the generic formula are of 5' $X_1X_2X_3SUG$ 3' (first terminal stretch of nucleotides) and 5' $CASX_4X_5X_6$ 3' (second stretch of nucleotides), wherein
a) $X_1$ is absent, $X_2$ is absent, $X_3$ is S, $X_4$ is S, $X_5$ is C, and $X_6$ is absent or
b) $X_1$ is absent, $X_2$ is G, $X_3$ is S, $X_4$ is S, $X_5$ is absent, and $X_6$ is absent,
c) $X_1$ is absent, $X_2$ is absent, $X_3$ is S, $X_4$ is S, $X_5$ is absent, and $X_6$ is absent,
wherein preferably
a) the first terminal stretch of nucleotides comprises a nucleotide sequence of 5' CGUG 3' and the second terminal stretch of nucleotides comprises a nucleotide sequence of 5' CACG 3' (see 215-F9-003) or
b) the first terminal stretch of nucleotides comprises a nucleotide sequence of 5' GCUG 3' and the second terminal stretch of nucleotides comprises a nucleotide sequence of 5' CAGC 3' (see 215-F9-008) or
c) the first terminal stretch of nucleotides comprises a nucleotide sequence of 5' GGUG 3' and the second terminal stretch of nucleotides comprises a nucleotide sequence of 5' CACC 3' (see 215-F9-009),
more preferably
the first terminal stretch of nucleotides comprises a nucleotide sequence of 5' CGUG 3' and the second terminal stretch of nucleotides comprises a nucleotide sequence of 5' CACG 3' (see 215-F9-003).

Combining the first terminal stretches of nucleotides and the second terminal stretches of nucleotides of S1P binding nucleic acids with three to four nucleotides the generic formula are of 5' $X_1X_2X_3SUG$ 3' (first terminal stretch of nucleotides) and 5' $CASX_4X_5X_6$ 3' (second stretch of nucleotides), wherein $X_1$ is absent, $X_2$ is absent, $X_3$ is S or absent, $X_4$ is S or absent, $X_5$ is absent, and $X_6$ is absent,
wherein preferably
the first terminal stretch of nucleotides comprises a nucleotide sequence of 5' GUG 3' and the second terminal stretch of nucleotides comprises a nucleotide sequence of 5' CAC 3' (see 215-F9-009).

In order to prove the functionality of S1P binding nucleic acids, spiegelmers 215-F9-001, 215-F9-002 were synthesized as spiegelmers comprising an amino-group at its 5'-end. To the amino-modified spiegelmers 215-F9-001-5'-Amino and 215-F9-002-5'-Amino a 40 kDa PEG-moiety was coupled leading to S1P binding spiegelmers 215-F9-001-5'-PEG (also referred to as NOX-S92) and 215-F9-002-5'-PEG (also referred to as NOX-S91). Synthesis and PEGylation of the spiegelmer is described in Example 2.

Figure 4:
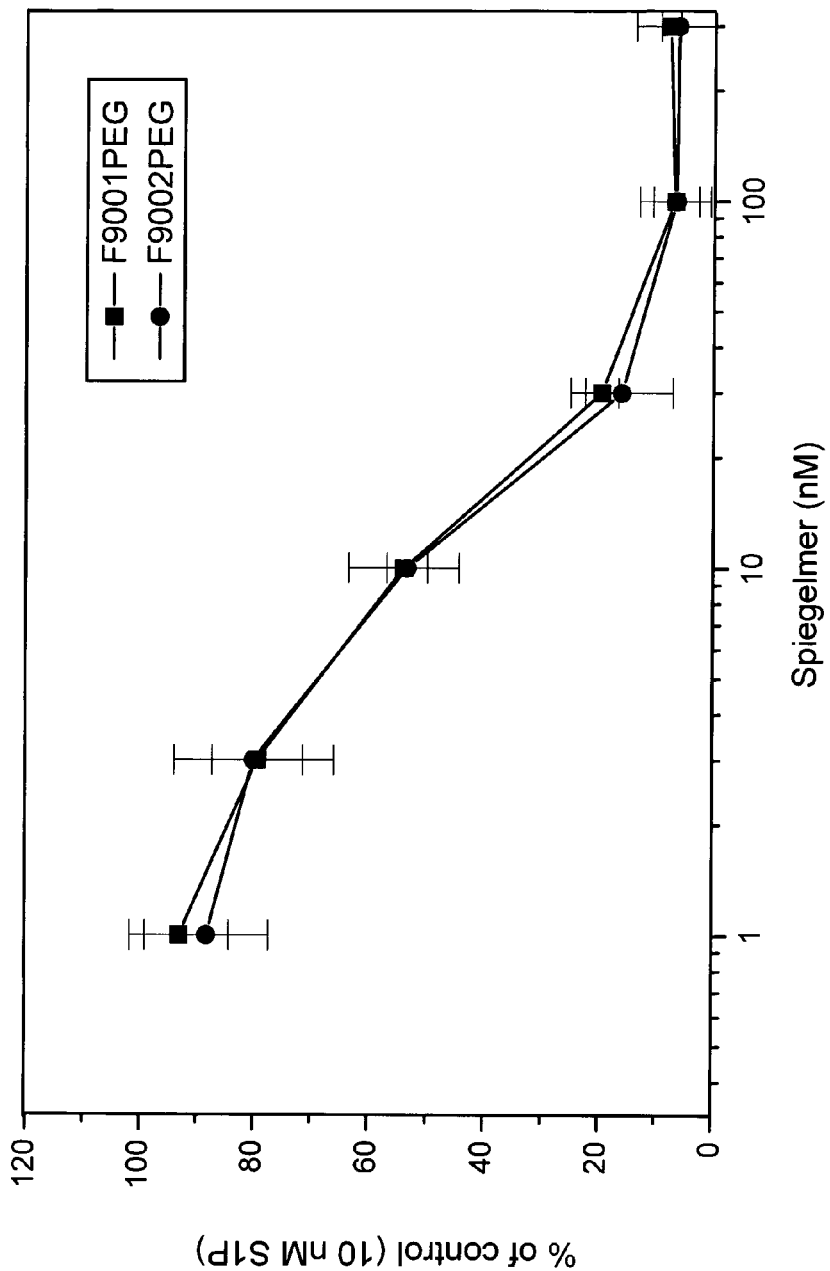
FIG. 4 shows the effect of the Spiegelmer 215-F9-001-5'-PEG (also referred to as NOX-S92) and 215-F9-002-5'-PEG (also referred to as NOX-S91) on S1P activity in an in vitro cell culture inhibition assay with the EDG3 receptor.
Figure 5:
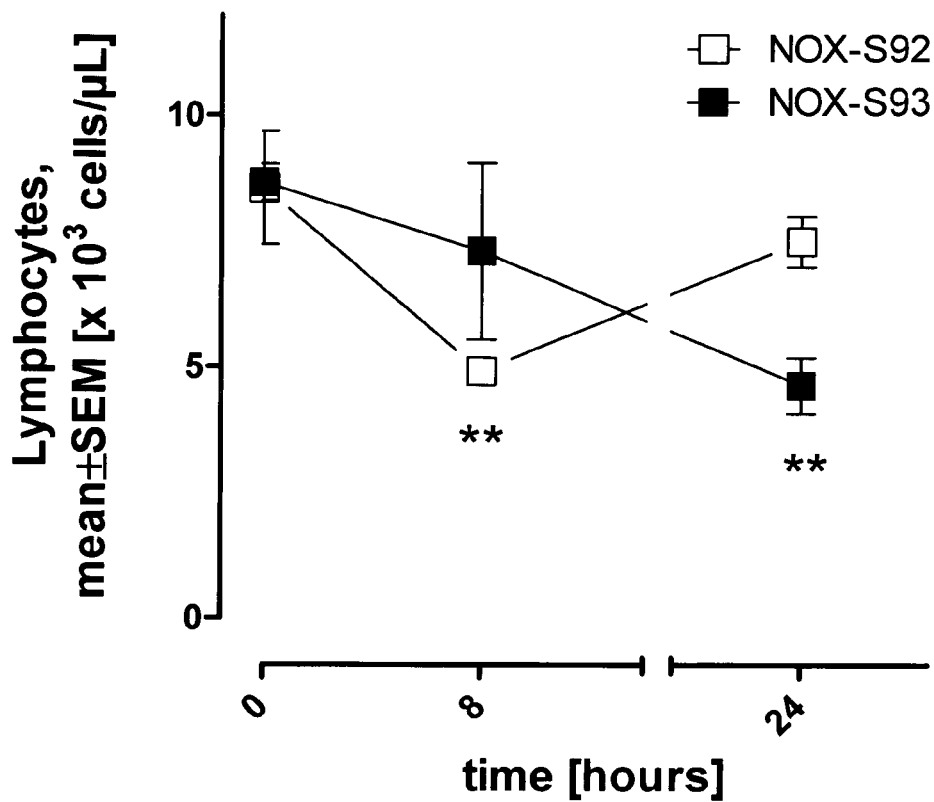
FIG. 5 shows the effect of the Spiegelmer NOX-S92 (also referred to as 215-F9-001-5'-PEG) and NOX-S93 (also referred to as 215-F9-002-D01-19-21-32-5'-PEG) on S1P activity in vivo, whereby NOX-S92 and NOX-S93 induced a lymphopenia due to binding to S1P.

S1P binding spiegelmers were tested to inhibit/antagonize the function of S1P in vitro and in vivo. As shown in Example 4, S1P binding spiegelmers inhibit the interaction and signalling of S1P to the receptors EDG-3/S1P$_3$ and EDG-1/S1P$_1$ in vitro (FIGS. 4 and 9). As shown in Example 7, S1P binding spiegelmers 215-F9-002-5'-PEG (also referred to as NOX-S91) inhibits angiogenesis in vitro. The efficacy of spiegelmer 215-F9-001-5'-PEG (also referred to as NOX-S92) was tested in vivo, wherein 215-F9-001-5'-PEG (also referred to as NOX-S92) induced a lymphopenia due to binding to S1P (Example 5, FIG. 5).

1.2 Increased Affinity of S1P-Binding Nucleic Acid 215-F9-002 by Replacement of Ribonucleotides by 2'-Deoxyribonucleotide The spiegelmer 215-F9-002 (also referred to as L-S1P-215-F9-002) binds S1P with an affinity of 31.5±3.1 nM (n=4) as determined by competitive spiegelmer pull-down assays (protocol see Example 6, FIG. 6).

The inventors surprisingly observed that the binding affinity of S1P binding spiegelmer L-S1P-215-F9-002 was improved by replacing ribonucleotides by 2'-deoxyribonucleotides, in particular that replacing ribonucleotides by 2'-deoxyribonucleotides at four positions in S1P binding spiegelmer L-S1P-215-F9-002 resulted in more than five-fold improved binding affinity. The inventors have surprisingly found that replacing one ribonucleotide by one 2'-deoxyribonucleotide in the sequence of spiegelmer L-S1P-215-F9-002 resulted in improved binding affinity to biotinylated D-e-S1P (see FIG. 6; spiegelmers L-S1P-215-F9-002-D01, L-S1P-215-F9-002-D11, L-S1P-215-F9-002-D19, L-S1P-215-F9-002-D21, L-S1P-215-F9-002-D22 and L-S1P-215-F9-002-D32). For spiegelmers L-S1P-215-F9-002-D19 and L-S1P-215-F9-002-D21 an improvement in binding affinity to biotinylated D-e-S1P by a factor of two to three was observed (FIGS. 6 and 7). Replacing one ribonucleotide by one 2'-deoxyribonucleotide at position 19 or at position 21 resulted in an improved of binding affinity of 16 nM (n=2) and 11.3±2.1 nM (n=3), respectively (FIG. 6).

In order to assess whether, starting from single nucleotide replacements which proved to be suitable to increase binding affinity, replacing more than one ribonucleotide by more than 2'-deoxyribonucleotide in the sequence of S1P binding spiegelmer L-S1P-215-F9-002 would result in further improvement in binding affinity to D-e-S1P, spiegelmers consisting of ribonucleotides and two up to five 2'-deoxyribonucleotides were synthesized: L-S1P-215-F9-002-D21-22, L-S1P-215-F9-002-D21-19, L-S1P-215-F9-002-D21-19-22, L-S1P-215-F9-002-D01-19-21-32 and L-S1P-215-F9-002-01-11-19-21-32 (FIG. 6). Competitive spiegelmer pull-down ranking assays showed that replacing ribonucleotides by 2'-deoxyribonucleotides at multiple positions of the L-S1P-215-F9-002 spiegelmer, whereby each of said positions as such has proven to be suitable to increase binding affinity, results in further improvement of binding affinity in comparison to derivatives of spiegelmer L-S1P-215-F9-002 comprising only one 2'-deoxyribonucleotide or two 2'-deoxyribonucleotides (FIGS. 6 and 7). However, replacing two ribonucleotides by two 2'-deoxyribonucleotides as shown for spiegelmer L-S1P-215-F9-002-D21-19 resulted in an improved binding affinity in comparison to spiegelmer L-S1P-215-F9-002-D21. This effect was not observed for spiegelmer L-S1P-215-F9-002-D21-22 also comprising two 2'-deoxyribonucleotides (FIGS. 6 and 8). Replacing three ribonucleotides by three 2'-deoxyribonucleotides (see spiegelmer L-S1P-215-F9-002-D21-19-22) did not result in further improved binding affinity in comparison to spiegelmer L-S1P-215-F9-002-D21-19 (FIGS. 6 and 8). However, for spiegelmer L-S1P-215-F9-002-D01-19-21-32 comprising four 2'-deoxyribonucleotides improved binding affinity to D-e-S1P in comparison to L-S1P-215-F9-002-D21-19 with two 2'-deoxyribonucleotides was observed (FIGS. 6 and 8). In competitive spiegelmer pull-down assays L-S1P-215-F9-002-D01-19-21-32 showed a binding affinity of 5.4 nM (n=2) (FIG. 6). Replacing five ribonucleotides by five 2'-deoxyribonucleotides (see spiegelmer L-S1P-215-F9-002-D01-11-19-21-32, FIG. 6) did not result in further improvement in binding to D-e-S1P (FIGS. 6 and 8). In summary, the inventors surprisingly observed that the binding affinity of D-e-S1P binding spiegelmer L-S1P-215-F9-002 was improved by a factor of more than five by replacing ribonucleotides by 2'-deoxyribonucleotides at the position 1, 19, 21 and 32 (see spiegelmer L-S1P-215-F9-002-D01-19-21-32, FIG. 6).

In vitro cell-culture assays (protocol see Example 4) confirmed that improved affinity to D-e-S1P translates into an enhanced inhibition of S1P function. 5'-40 kDa-PEG-L-S1P-215-F9-002 (also referred to as NOX-S91) and 5'-40 kDa-PEG-L-S1P-215-F9-002-D01-19-21-32 (also referred to as NOX-S93) inhibited S1P-induced arrestin recruitment in a reporter cell line expressing human S1P-receptor EDG1 with $IC_{50}$ values of 22.5 nM and 10.3 nM, respectively (FIGS. 9A, 9B). In a cell line expressing human S1P-receptor EDG3 5'-40 kDa-PEG-L-S1P-215-F9-002 (also referred to as NOX-S91) and 5'-40 kDa-PEG-L-S1P-215-F9-002-D01-19-21-32 (also referred to as NOX-S93) inhibited S1P-induced calcium release with $IC_{50}$ values of 10 nM and 5.5 nM, respectively (FIGS. 9C, 9D).

The S1P binding spiegelmers 5'-40 kDa-PEG-L-S1P-215-F9-002 (also referred to as NOX-S91) and 5'-40 kDa-PEG-L-S1P-215-F9-002-D01-19-21-32 (also referred to as NOX-S93) were successfully tested in an in vitro angiogenesis assay (see Example 7, FIG. 10). The S1P binding spiegelmers 5'-40 kDa-PEG-L-S1P-215-F9-001 (also referred to as NOX-S92) and 5'-40 kDa-PEG-L-S1P-215-F9-002-D01-19-21-32 (also referred to as NOX-S93) were successfully tested in in vivo studies (see Examples 5, FIG. 5).

EXAMPLE 2

Synthesis and Derivatization of Aptamers and Spiegelmers

Small Scale Synthesis

Aptamers (D-RNA nucleic acids or D-DNA modified D-RNA nucleic acids) and spiegelmers (L-RNA nucleic acids or L-DNA modified L-RNA nucleic acids) were produced by solid-phase synthesis with an ABI 394 synthesizer (Applied Biosystems, Foster City, Calif., USA) using 2'TBDMS RNA and DNA phosphoramidite chemistry with standard exocyclic amine protecting groups (Damha and Ogilvie, 1993). For the RNA part of the oligonucleotide rA(N-Bz)-, rC(N—Ac)—, rG(N-ibu)-, and rU-phosphoramidites in the D- and L-configuration were used, while for the DNA part dA(N-Bz)-, dC(N—Ac)—, dG(N-ibu)-, and dT in the D- and L-configuration were applied. All phosphoramidites were purchased from ChemGenes, Wilmington, Mass. After synthesis and deprotection aptamers and spiegelmers were purified by gel electrophoresis.

Large Scale Synthesis Plus Modification

Spiegelmers were produced by solid-phase synthesis with an ÄktaPilot100 synthesizer (GE Healthcare, Freiburg) using 2'TBDMS RNA and DNA phosphoramidite chemistry with standard exocyclic amine protecting groups (Damha and Ogilvie, 1993). L-rA(N-Bz)-, L-rC(N—Ac)—, L-rG(N-ibu)-, L-rU-, L-dA(N-Bz)-, L-dC(N—Ac)—, L-dG(N-ibu)-, and L-dT-phosphoramidites were purchased from ChemGenes, Wilmington, Mass. The 5'-amino-modifier was purchased from American International Chemicals Inc. (Framingham, Mass., USA). Synthesis of the unmodified or a 5'-Amino-modified spiegelmer was started on L-riboA, L-riboC, L-riboG, L-riboU, L-2'deoxyA, L-2'deoxyC, L-2'deoxyG, or L-2'deoxyT modified CPG pore size 1000 Å (Link Technology, Glasgow, UK. For coupling of the RNA and DNA phosphoramidites (15 min per cycle), 0.3 M benzylthiotetrazole (CMS-Chemicals, Abingdon, UK) in acetonitrile, and 2 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott et al., 1995) using Sourcel5RPC medium (Amersham). The 5'DMT-group was removed with 80% acetic acid (30 min at RT). In case of 5'aminomodified Spiegelmers the 5'MMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation of Spiegelmers

In order to prolong the Spiegelmer's plasma residence time in vivo, a 40 kDa polyethylene glycol (PEG) moiety was covalently coupled at the 5'-end of the spiegelmers.

5'-PEGylation of Spiegelmers

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 11; pH=8.4 was adjusted with 1 M HCl).

The pH of the Spiegelmer solution was brought to 8.4 with 1 M NaOH. Then, 40 kDa PEG-NHS ester (Jenkem Technology, Allen, Tex., USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3

Analysis of S1P Binding Aptamers by Pull-Down Binding Assays

Direct Pull-Down Assay

The affinity of S1P binding nucleic acids was measured in a pull down assay format at 37° C. using aptamers (D-RNA nucleic acids) and biotinylated L-e-S1P. Aptamers were radioactively labeled at the 5'-end by T4 polynucleotide kinase (Invitrogen, Karlsruhe, Germany) using [$\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 300 pM concentration at 37° C. in selection buffer (20 mM Tris-HCl pH 7.4; 150 mM NaCl; 5 mM KCl; 1 mM $MgCl_2$; 1 mM $CaCl_2$; 0.1% [w/vol] Tween-20; 4 mg/ml bovine serum albumin) together with varying amounts of biotinylated L-e-S1P for 3-12 hours in order to reach equilibrium at low concentrations. Selection buffer was supplemented with 10 µg/ml yeast RNA (Ambion, Austin, USA) in order to prevent adsorption of binding partners to surfaces of the used plasticware or the immobilization matrix. The concentration range of biotinylated L-e-S1P was set from 192 pM to 3000 nM; total reaction volume was 0.1 ml. Biotinylated L-e-S1P and complexes of aptamers and biotinylated L-e-S1P were immobilized on 2 µl Streptavidin Ultralink Plus beads (Pierce Biotechnology, Rockford, USA) which had been preequilibrated with selection buffer before addition to the binding reactions. Beads were kept in suspension for 20 mM at the respective temperature in a thermomixer to immobilize biotinylated L-e-S1P and the complexes of biotinylated L-e-S1P and bound aptamers. Immobilized radioactivity was quantitated in a scintillation counter after detaching the supernatant and appropriate washing. The percentage of binding or normalized binding was plotted against the concentration of biotinylated L-e-S1P and dissociation constants were obtained using software algorithms (GRAFIT; Erithacus Software; Surrey U.K.) assuming a 1:1 stoichiometry.

Competitive Pull-Down Assay

Another pull-down assay format was used for the determination of affinity constants of S1P binding nucleic acids by competition of a labeled aptamer with varying amounts of a non-labeled aptamer. The non-labeled aptamer competed with the labeled aptamer for binding to biotinylated L-e-S1P, thus decreasing the binding signal according to the affinity of the aptamer to L-e-S1P. The assay was performed at 37° C. with 150 pM radioactively labeled aptamer together with a constant amount of 20 nM biotinylated L-e-S1P in 0.4 ml selection buffer for 3-12 hours. These conditions resulted in around 5-10% binding to the biotinylated L-S1P after immobilization and washing on NeutrAvidin agarose or Streptavidin Ultralink Plus (both from Pierce). For competition non-labeled aptamers were added together with the constant amount of a labeled aptamer in a concentration range from 96 pm to 1500 nM to the binding reactions. After completion of binding, immobilization, appropriate washing and determination of immobilized radioactivity on the beads the percentage of binding or normalized binding was determined and plotted against the concentration of non-labeled aptamer. Dissociation constants were obtained using software algorithms (see above) assuming a 1:1 stoichiometry.

The same assay format was used for comparative ranking of a set of different aptamers however with the exception that instead of a full concentration range only three different concentrations of each non-labeled aptamer (e.g. 5, 50, 500 nM) were applied to the test tube together with one labeled aptamer that served as a reference. The aptamer that was found most active in the test could then serve as a new reference for comparative analysis of further aptamer variants.

EXAMPLE 4

S1P In Vitro Cell-Culture Assays 4.1 Inhibition of S1P-Induced Calcium-Release by S1P-Binding Spiegelmers.

Stable transfected CHO-cells expressing the human S1P3 receptor (EDG3/S1P$_3$) and the human G-Protein $G_{\alpha 15}$ are seeded with $5 \times 10^4$ cells per well in a black 96 well-plate with clear bottom (Greiner) and cultivated overnight at 37° C. and 5% $CO_2$ in UltraCHO medium (Lonza) which contained in addition 100 units/ml penicillin, 100 µg/ml streptomycin and 10 µg/ml blasticidin.

The stimulation solutions (D-e-S1P+various concentrations of spiegelmer) are made up as 10× concentrated solutions in UltraCHO medium containing 20 mM HEPES and 5 mM Probenecid (CHO—U+) in a 96 well "low profile" PCR plate. The solutions are mixed thoroughly and incubated on a thermomixer at 37° C. for 30 to 60 min. In each (vertical) row a buffer control (no D-e-S1P) and a D-e-S1P control (no spiegelmer) are included.

Before loading with the calcium indicator dye FluoForte (Enzo Life Sciences), cells are washed once with 200 µl CHO—U+. Then 90 µl of the indicator dye solution (5.56 µg/ml FluoForte, 0.044% pluronic 127 (Invitrogen) in CHO—U+) are added and the cells are incubated for 60 min at 37° C.

Measurement of fluorescence signals is done at an excitation wavelength of 485 nm and an emission wavelength of 520 nm in a Fluostar Optima multidetection plate reader (BMG).

For the parallel analysis of several samples, wells of one column (vertical row) of a 96 well plate are recorded together.

The measurement is started by reading 3 values for baseline determination. Then the measurement is interrupted and the plate is moved out of the instrument. 10 µl of the stimulation solutions of one row from the "low profile" plate are added to the wells of the row to be stimulated with the aid of a multi-channel pipette. After mixing (gently swivelling the plate) the plate is returned into the instrument and the measurement is continued (20 measurements in total with 4 sec intervals).

For each well the difference between maximal fluorescence and base line value is determined and plotted against spiegelmer concentration. In most cases the value for the sample without spiegelmer (D-e-S1P only) is set 100% and the values for the samples with spiegelmer are calculated as percent of this. For a dose-response curve the percent-values are plotted against spiegelmer concentration and the $IC_{50}$-value (concentration of spiegelmer at which 50% of the activity without spiegelmer is present) is determined graphically from the resulting curve.

To show the efficacy of anti-S1P-spiegelmers, cells were stimulated with 10 nM D-e-S1P or D-e-S1P preincubated with various amounts of spiegelmers 215-F9-001-5'-PEG (also referred to as NOX-S92) and 215-F9-002-5'-PEG (also referred to as 5'-40 kDa-PEG-L-S1P-215-F9-002 and NOX-S91) or with various amounts of 215-F9-002-5'-PEG (also referred to as 5'-40 kDa-PEG-L-S1P-215-F9-002 NOX-S91) and 5'-40 kDa-PEG-L-S1P-215-F9-002-D01-19-21-32 (also referred to as NOX-S93). The results show the percentage of fluorescence signal normalized to the signal obtained with no spiegelmer.

The spiegelmers 215-F9-001-5'-PEG (also referred to as NOX-S92) and 215-F9-002-5'-PEG (also referred to as 5'-40 kDa-PEG-L-S1P-215-F9-002 and NOX-S91) were found to inhibit S1P-induced $Ca^{++}$-release with an $IC_{50}$ of about 10 nM (Means +/− std.dev. from three independent experiments) (FIGS. 4 and 9C). Spiegelmer 5'-40 kDa-PEG-L-S1P-215-F9-002-D01-19-21-32 (also referred to as NOX-S93) was found to inhibit S1P-induced $Ca^{++}$-release with an $IC_{50}$ of about 5.5 nM (FIG. 9D).

4.2 Inhibition of β-Arrestin Recruitment Induced by S1P via EDG1 Receptor by S1P-Binding Spiegelmers PathHunter™ eXpress EDG-1 CHO—K1 β-arrestin GPCR cells (DiscoverX) were seeded at $1\times10^4$ cells per well in a white 96 well-plate with clear bottom (Greiner) and cultivated for 48 h at 37° C. and 5% $CO_2$ in 100 µl Culture Medium (DiscoverX). Stimulation solutions (D-e-S1P+various concentrations of Spiegelmer) are made up as 11× concentrated solutions in HBSS (Gibco) supplemented with 1 mg/ml BSA and 20 mM HEPES, mixed thoroughly and incubated at 37° C. for 30 min. 10 µl stimulation solution were added per well (triplicates) and cells were incubated for 90 min at 37° C. and 5% $CO_2$.

Upon receptor activation by D-e-S1P, the interaction of activated EDG1 with β-arrestin leads to β-galactosidase enzyme fragment complementation.

For quantification of β-galactosidase activity 55 µl Working Detection Reagent Solution (DiscoverX) were added and incubated for 90 min at room temperature. Luminescence was subsequently measured in a Fluostar Optima multidetection plate reader (BMG).

To show the efficacy of anti-S1P-spiegelmers, cells were stimulated with 10 nM D-e-S1P or D-e-S1P preincubated with various amounts of 215-F9-002-5'-PEG (also referred to as 5'-40 kDa-PEG-L-S1P-215-F9-002 or NOX-S91) and 5'-40 kDa-PEG-L-S1P-215-F9-002-D01-19-21-32 (NOX-S93). The results show the percentage of luminescence signal normalized to the signal obtained without addition of spiegelmer. Mean values±SD from triplicate cultures are shown.

5'-40 kDa-PEG-L-S1P-215-F9-002 (also referred to as 215-F9-002-5'-PEG and NOX-S91) and 5'-40 kDa-PEG-L-S1P-215-F9-002-D01-19-21-32 (also referred to as NOX-S91) inhibited S1P(D-e-S1P)-induced arrestin recruitment in a reporter cell line expressing human S1P-receptor EDG1 with $IC_{50}$ values of 22.5 nM and 10.3 nM, respectively (FIGS. 9A, 9B).

EXAMPLE 5

Activity of S1P Binding Spiegelmers In Vivo

A pharmacodynamic study designed to test the ability of spiegelmers NOX-S92 or NOX-S93 to alter lymphocyte trafficking in mice was performed. Five adult female mice per group and time point, with 20-28 g body weight (bw) received an intravenous bolus injection (10 mL/kg bw) into the tail vein. The injected dose of spiegelmers NOX-S92 or NOX-S93 was 20 mg/kg bw and 5% glucose for injection was used as vehicle. At the indicated time points EDTA-blood samples were withdrawn to determine the lymphocyte count with the scil Vet abc hematology analyzer (scil animal care company). Treatment with spiegelmers NOX-S92 or NOX-S93 induced a lymphopenia as indicated by a reduction from basal levels of 8.6 to $4.9\times10^3$ lymphocytes/µL (NOX-S92) after eight hours or from 8.7 to $4.6\times10^3$ lymphocytes/µL blood (NOX-S93) twenty-four hours post application (see FIG. 5).

Significance was determined using Dunntett's Multiple Comparison Test.

EXAMPLE 6

Competitive Spiegelmer Pull-Down Assay

Affinity constants of S1P binding spiegelmers were determined by competitive pull-down assays. In order to allow for radioactive labeling of the spiegelmer by T4 polynucleotide kinase two guanosine residues in the D-configuration were added to the 5'-end of the L-S1P-215-F9-002 spiegelmer. Unlabeled spiegelmers were then tested for their ability to compete with 300-600 pM radiolabeled spiegelmer L-S1P-215-F9-002-5'diD-G for binding to a constant amount of biotinylated D-e-S1P, i.e. decreasing the binding signal according to the binding affinity of the non-labeled spiegelmer to D-e-S1P. D-e-S1P was used at a concentration of 8 nM resulting in a final binding of approximately 10% of radiolabeled spiegelmer L-S1P-215-F9-002-5'diD-G in the absence of competitor spiegelmers. Assays were performed in 250 μl selection buffer (20 mM Tris-HCl pH 7.4; 150 mM NaCl; 5 mM KCl; 1 mM MgCl$_2$; 1 mM CaCl$_2$; 0.1% [w/vol] Tween-20; 4 mg/ml bovine serum albumin; 10 μg/ml Yeast-RNA) for 3-4 hours at 37° C. Biotinylated D-e-S1P and complexes of spiegelmer and biotinylated S1P were immobilized on 5 μl Neutravidin Ultralink Plus beads (Pierce Biotechnology, Rockford, USA) which had been pre-equilibrated with selection buffer before addition to the binding reactions. Beads were kept in suspension for 30 min at 37° C. in a thermomixer. After removal of supernatants and appropriate washing, immobilized radioactivity was quantified in a scintillation counter. The percentage of binding or normalized percentage of bound radiolabeled spiegelmer L-S1P-215-F9-002-5'diD-G was plotted against the corresponding concentration of competitor spiegelmer. Dissociation constants were obtained using GraphPad Prism software. The same assay format was used for comparative ranking of a set of different spiegelmers. In this case competitor spiegelmers were used at a single concentration as indicated.

EXAMPLE 7

NOX-S91 and NOX-S93 Inhibit Angiogenesis In Vitro

The spiegelmers NOX-S91 and NOX-S93 were tested for their ability to inhibit VEGF-A (Vascular Endothelial Growth Factor-A) and S1P (sphingosine-1-phosphate) induced sprouting of human umbilical vein endothelial cells (HUVEC) in the spheroid-based cellular angiogenesis assay in vitro.

The experiments were pursued in modification of the originally published protocol (Korff and Augustin, J Cell Sci 112: 3249-58, 1999). In brief, spheroids were prepared as described (Korff and Augustin, J Cell Biol 143: 1341-52, 1998) by pipetting 500 HUVEC in a hanging drop on plastic dishes to allow overnight spheroid aggregation. 50 HUVEC spheroids were then seeded in 0.9 ml of a collagen gel and pipetted into individual wells of a 24 well plate to allow polymerization.

The angiogenesis stimulators S1P [100 nM final assay concentration] or VEGF-A [25 ng/mL final assay concentration] were added after 30 min by pipetting 100 μl of a 10-fold concentrated working dilution on top of the polymerized gel. Likewise a dose-range (10 nM-10 μM in half-log increments) of the S1P-binding spiegelmers was added to allow the calculation of an IC50. Vehicle only and either angiogenesis stimulator alone plus spiegelmer vehicle served as control wells (basal sprouting and maximal sprouting induction). Sunitinib was used as a positive control substance in the VEGF-induced sprouting assay. Plates were incubated at 37° C. for 24 hours and fixed by adding 4% Roti-Histofix. Sprouting intensity of treated HUVEC spheroids was quantified by determining the cumulative sprout length per spheroid using an image analysis system consisting of an inverted microscope and the digital imaging software Analysis 3.2 (Soft imaging system, Münster, Germany). The mean of the cumulative sprout length of 10 randomly selected spheroids was analyzed as an individual data point. IC50 determination was done with GraphPad Prism version 5.02 software with constrain of bottom to 0 and top to 100 using a nonlinear regression curve fit with variable hill slope. The equation is a four-parameter logistic equation. For calculation the median of basal sprouting was subtracted from all other data points. The median control VEGF-A or S1P sprouting was set to 100%.

Both NOX-S91 and NOX-S93 inhibited sprouting that was induced by either S1P or VEGF-A. NOX-S93 showed stronger inhibition in S1P induced EC sprouting than NOX-S91. In the S1P-induced sprouting assay NOX-S93 showed a stronger inhibition (3.4×10 7 M) than NOX-S91 (7.5×10 7 M). Both drugs exhibited lower IC50 values in the VEGF-A-induced sprouting (see FIG. 10). The IC50 values for NOX S91 and NOX-S93 were 2.1×10-7 M and 2.4×10-7 M on VEGF-A induced EC sprouting. Sunitinib was used as positive control and showed inhibition of HUVEC sprouting in the same range with an IC$_{50}$ value of 2.5×10-7 M (see FIG. 10).

The tested Spiegelmers inhibited S1P or VEGF-A induced EC sprouting in the cellular angiogenesis assay. These results are in agreement with data published for an S1P-antibody (Visentin et al, Cancer Cell 2006 9(3):225-38).

The features of the present invention disclosed in the specification, the claims, the sequence listing and/or the drawings may both separately and in any combination thereof be material for realizing the invention in various forms thereof.

The invention claimed is:

1. An L-nucleic acid molecule that binds sphingosine 1-phosphate, wherein the L-nucleic acid molecule comprises in 5'→3' direction, (a) a first terminal stretch of nucleotides, a central stretch of nucleotides and a second terminal stretch of nucleotides, or (b) the second terminal stretch of nucleotides, the central stretch of nucleotides and the first terminal stretch of nucleotides, wherein the first terminal stretch of nucleotides comprises three to six nucleotides, and the second terminal stretch of nucleotides comprises three to six nucleotides, and the central stretch of nucleotides comprises

```
                                        (SEQ ID NO: 43)
5' AAUAGCCGUUGAAACGCCUUUAGAGAAGCACUAG 3', (SEQ ID NO: 44)
5' AAUAGCCGAUGAAACGCCUUUAGAGAAGCACUAG 3'
or
                                        (SEQ ID NO: 45)
5' AAUAGCCGAAUGAAACGCCUUAAGAGAAGCACUAG 3'.
```

2. The L-nucleic acid molecule according to claim 1, wherein the L-nucleic acid molecule is an antagonist of an activity mediated by sphingosine 1-phosphate.

3. The L-nucleic acid molecule according to claim 1, wherein the first terminal stretch of nucleotides comprises 5' $X_1X_2X_3$SUG 3' and the second terminal stretch of nucleotides comprises 5' CAS$X_4X_5X_6$ 3', wherein
a) $X_1$ is A, $X_2$ is G, $X_3$ is S, $X_4$ is S, $X_5$ is C, and $X_6$ is U;
b) $X_1$ is absent, $X_2$ is G, $X_3$ is S, $X_4$ is S, $X_5$ is C, and $X_6$ is U;
c) $X_1$ is A, $X_2$ is G, $X_3$ is S, $X_4$ is S, $X_5$ is C, and $X_6$ is absent; or
d) $X_1$ is absent, $X_2$ is G, $X_3$ is S, $X_4$ is S, $X_5$ is C, and $X_6$ is absent.

4. The L-nucleic acid molecule according to claim 1, wherein
a) the first terminal stretch of nucleotides comprises 5' AGCGUG 3' and the second terminal stretch of nucleotides comprises 5' CACGCU 3'; or
b) the first terminal stretch of nucleotides comprises 5' GCGUG 3' and the second terminal stretch of nucleotides comprises 5' CACGC 3'.

5. The L-nucleic acid molecule according to claim 1, wherein the first terminal stretch of nucleotides comprises 5' $X_1X_2X_3$SUG 3' and the second terminal stretch of nucleotides comprises a nucleotide sequence of 5' CAS$X_4X_5X_6$ 3', wherein
a) $X_1$ is absent, $X_2$ is absent, $X_3$ is S, $X_4$ is S, $X_5$ is C, and $X_6$ is absent;
b) $X_1$ is absent, $X_2$ is G, $X_3$ is S, $X_4$ is S, $X_5$ is absent, and $X_6$ is absent; or
c) $X_1$ is absent, $X_2$ is absent, $X_3$ is S, $X_4$ is S, $X_5$ is absent, and $X_6$ is absent.

6. The L-nucleic acid molecule according to claim 1, wherein
a) the first terminal stretch of nucleotides comprises 5' CGUG 3' and the second terminal stretch of nucleotides comprises 5' CACG 3';
b) the first terminal stretch of nucleotides comprises 5' GCUG 3' and the second terminal stretch of nucleotides comprises 5' CAGC 3'; or
c) the first terminal stretch of nucleotides comprises 5' GGUG 3' and the second terminal stretch of nucleotides comprises 5' CACC 3'.

7. The L-nucleic acid molecule according to claim 1, wherein the first terminal stretch of nucleotides comprises 5' $X_1X_2X_3$SUG 3' and the second terminal stretch of nucleotides comprises 5' CAS$X_4X_5X_6$ 3', wherein $X_1$ is absent, $X_2$ is absent, $X_3$ is S or absent, $X_4$ is S or absent, $X_5$ is absent, and $X_6$ is absent.

8. The L-nucleic acid molecule according to claim 1, wherein the first terminal stretch of nucleotides comprises 5' GUG 3' and the second terminal stretch of nucleotides comprises 5' CAC 3'.

9. The L-nucleic acid molecule according to claim 1, comprising a nucleotide sequence according to any one of SEQ ID NOs:12 to 26, 41 or 42, or a nucleic acid molecule at least 85% homologous thereto.

10. The L-nucleic acid molecule according to claim 1, wherein the L-nucleic acid molecule comprises a modification group, wherein the L-nucleic acid molecule comprising the modification group gas a decreased excretion rate from an organism as compared to the nucleic acid not comprising the modification group; or the L-nucleic acid molecule comprising, the modification group has an increased retention time in an organism as compared to the nucleic acid molecule not comprising the modification group.

11. The L-nucleic acid molecule according to claim 10, wherein the modification group is selected from the group consisting of a biodegradable modification and a non-biodegradable modification.

12. The L-nucleic acid of claim 10, wherein the modification group is selected from the group consisting of polyethylene glycol, linear polyethylene glycol, branched polyethylene glycol, hydroxyethyl starch, a peptide, a protein, a polysaccharide, a sterol, polyoxypropylene, polyoxyamidate and poly (2-hydroxyethyl)-L-glutamine.

13. The L-nucleic acid molecule according to claim 10, wherein the modification group comprises a linear polyethylene glycol or a branched polyethylene glycol comprising a molecular weight of 20,000 to about 120,000 Da, 30,000 to about 80,000 Da or about 40,000 Da.

14. The L-nucleic acid molecule according to claim 10, wherein the modification group comprises hydroxyethyl starch comprising a molecular weight of from about 50 to about 1000 kDa, from about 100 to about 700 kDa or from 200 to 500 kDa.

15. The L-nucleic acid molecule according to claim 10, wherein the modification group is coupled to the L-nucleic acid molecule via a biodegradable linker or a non-biodegradable linker.

16. A method comprising administering to a host suspected of a disease associated with sphingosine 1-phosphate, the L-nucleic acid molecule according to claim 1.

17. The method according to claim 16, wherein said L-nucleic acid inhibits angiogenensis, proliferation and/or fibrogenesis.

18. The method according to claim 16, wherein said disease comprises an ocular disease.

19. The method of claim 16, wherein said disease is selected from the group consisting of age-related macular degeneration, diabetic retinopathy with diabetic macular edema, retinal pigmented epithelium (RPE) detachment in age-related macular degeneration, RPE detachment in diabetic retinopathy, proliferative vitreoretinopathy, retinal fibrosis in age-related macular degeneration and retinal fibrosis in diabetic retinopathy.

20. The method according to claim 16, wherein said disease comprises cancer.

21. The method of claim 16, wherein said disease is selected from the group consisting of breast cancer, ovarian cancer, melanoma, lung cancer and hyperplasia.

22. The method according to claim 16, wherein said disease comprises inflammation.

23. The method of claim 16, wherein said disease is selected from the group consisting of an autoimmune disease, a pneumonia, sepsis and trauma.

24. The method according to claim 23, wherein said disease is selected from the group consisting of multiple sclerosis, rheumatoid arthritis, psoriasis, asthma and inflammatory bowel disease.

25. A pharmaceutical composition comprising the L-nucleic acid molecule as defined in claim 1 and a pharmaceutically acceptable excipient, a pharmaceutically acceptable carrier, a pharmaceutically active agent or combinations thereof.

26. A complex comprising the L-nucleic acid molecule according to claim 1 and sphingosine 1-phosphate.

27. An L-nucleic acid molecule that binds sphingosine 1-phosphate, wherein the L-nucleic acid molecule is at least 85% homologous to a target L-nucleic acid molecule consisting of SEQ ID NO:18, wherein the L-nucleic acid molecule comprises ribonucleotides and at least one deoxyribonucleotide.

28. The L-nucleic acid molecule according to claim 27, wherein the L-nucleic acid molecule comprises any one of SEQ ID NOs: 27 to 37, 39 or 40.

29. The L-nucleic acid molecule according to claim 27, wherein the L-nucleic acid molecule comprises a modification group, wherein excretion rate of the L-nucleic acid molecule comprising the modification group from an organism is decreased as compared to the nucleic acid not comprising the modification group; or the L-nucleic acid molecule comprising the modification group has an increased retention time in an organism as compared to the nucleic acid molecule not comprising the modification group.

30. The L-nucleic acid molecule according to claim 29, wherein the modification group is selected from the group consisting of a biodegradable modification and a non-biodegradable modification.

31. The L-nucleic acid of claim 29, wherein the modification group is selected from the group consisting of polyethylene glycol, linear polyethylene glycol, branched polyethylene glycol, hydroxyethyl starch, a peptide, a protein, a polysaccharide, a sterol, polyoxypropylene, polyoxyamidate and poly (2-hydroxyethyly)-L-glutamine.

32. The L-nucleic acid molecule according to claim 29, wherein the modification group comprises a linear polyethylene glycol or a branched polyethylene glycol comprising a molecular weight of 20,000 to about 120,000 Da, 30,000 to about 80,000 Da or about 40,000 Da.

33. The L-nucleic acid molecule according to claim 29, wherein the modification group comprises hydroxyethyl starch comprising a molecular weight of from about 50 to about 1000 kDa, from about 100 to about 700 kDa or from 200 to 500 kDa.

34. The L-nucleic acid molecule according to claim 29, wherein the modification group is coupled to the L-nucleic acid molecule via a biodegradable linker or a non-biodegradable linker.

\* \* \* \* \*

SEQUENCE LISTING

```
<160> NUMBER OF SEQ ID NOS: 45

<210> SEQ ID NO 1
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 1
agcgugaaua gccguugaaa cgccuuuaga gaagcacuag cacgcu            46

<210> SEQ ID NO 2
<211> LENGTH: 46
<212> TYPE: DNA
<213> ORGANISM: artificial
<220> FEATURE:
<223> OTHER INFORMATION: synthetic
```

```
<220> FEATURE:
<221> NAME/KEY: misc_feature
<223> OTHER INFORMATION: D-RNA

<400> SEQUENCE: 2 agcgugaauua gccgaugaaa cgccuuuaga gaagcacuag cacgcu          46

<210> SEQ ID NO 3
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 3 agcgugaauua gccgaaugaa acgccuuuag agaagcacua gcacgcu         47

<210> SEQ ID NO 4
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 4 agcgugaauua gccgaaugaa acgccuuaag agaagcacua gcacgcu         47

<210> SEQ ID NO 5
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 5
gcguguauag ccguugaaac gccuuuagag aagcacuagc acgc              44

<210> SEQ ID NO 6
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 6
gcgugaauag ccgaaugaaa cgccuuuaga gaagcacuag cacgc             45

<210> SEQ ID NO 7
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA
```

```
<400> SEQUENCE: 7
gcgugaauag ccguugaaac gccuuuagag aagcacuagc acgc              44

<210> SEQ ID NO 8
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 8
cgugaauagc cguugaaacg ccuuuagaga agcacuagca cg                42

<210> SEQ ID NO 9
<211> LENGTH: 40
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 9
gugaauagcc guugaaacgc cuuuagagaa gcacuagcac                   40

<210> SEQ ID NO 10
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 10
gcugaauagc cguugaaacg ccuuuagaga agcacuagca gc                42

<210> SEQ ID NO 11
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 11
ggugaauagc cguugaaacg ccuuuagaga agcacuagca cc                42

<210> SEQ ID NO 12
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 12
agcgugaaua gccguugaaa cgccuuuaga gaagcacuag cacgcu            46
```

```
<210> SEQ ID NO 13
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 13
agcgugaaua gccgaugaaa cgccuuuaga gaagcacuag cacgcu            46

<210> SEQ ID NO 14
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 14
agcgugaaua gccgaaugaa acgccuuuag agaagcacua gcacgcu           47

<210> SEQ ID NO 15
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 15
agcgugaaua gccgaaugaa acgccuuaag agaagcacua gcacgcu           47

<210> SEQ ID NO 16
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 16
gcguguauag ccguugaaac gccuuuagag aagcacuagc acgc              44

<210> SEQ ID NO 17
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 17
gcgugaauag ccgaaugaaa cgccuuuaga gaagcacuag cacgc             45

<210> SEQ ID NO 18
<211> LENGTH: 44
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 18
gcgugaauag ccguugaaac gccuuuagag aagcacuagc acgc                    44

<210> SEQ ID NO 19
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 19
cgugaauagc cguugaaacg ccuuuagaga agcacuagca cg                      42

<210> SEQ ID NO 20
<211> LENGTH: 40
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 20
gugaauagcc guugaaacgc cuuuagagaa gcacuagcac                         40

<210> SEQ ID NO 21
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 21
gcugaauagc cguugaaacg ccuuuagaga agcacuagca gc                      42

<210> SEQ ID NO 22
<211> LENGTH: 42
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 22
ggugaauagc cguugaaacg ccuuuagaga agcacuagca cc                      42

<210> SEQ ID NO 23
<211> LENGTH: 46
<212> TYPE: DNA
<213> ORGANISM: artificial
<220> FEATURE:
<223> OTHER INFORMATION: synthetic
```

-continued

```
<220> FEATURE:
<221> NAME/KEY: misc_feature
<223> OTHER INFORMATION: L-RNA

<400> SEQUENCE: 23
agcgugaaua gccguugaaa cgccuuuaga gaagcacuag cacgcu        46

<210> SEQ ID NO 24
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 24
gcgugaauag ccguugaaac gccuuuagag aagcacuagc acgc          44

<210> SEQ ID NO 25
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 25
agcgugaaua gccguugaaa cgccuuuaga gaagcacuag cacgcu        46

<210> SEQ ID NO 26
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 26
gcgugaauag ccguugaaac gccuuuagag aagcacuagc acgc          44

<210> SEQ ID NO 27
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (1)..(1)
<223> OTHER INFORMATION: 2' deoxyribonucleotide

<400> SEQUENCE: 27
gcgugaauag ccguugaaac gccuuuagag aagcacuagc acgc          44

<210> SEQ ID NO 28
<211> LENGTH: 44
<212> TYPE: DNA
<213> ORGANISM: artificial
<220> FEATURE:
<223> OTHER INFORMATION: synthetic
```

-continued

<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (11)..(11)
<223> OTHER INFORMATION: 2' deoxyribonucleotide

<400> SEQUENCE: 28
gcgugaauag ccguugaaac gccuuuagag aagcacuagc acgc        44

<210> SEQ ID NO 29
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (19)..(19)
<223> OTHER INFORMATION: 2' deoxyribonucleotide

<400> SEQUENCE: 29
gcgugaauag ccguugaaac gccuuuagag aagcacuagc acgc        44

<210> SEQ ID NO 30
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (21)..(21)
<223> OTHER INFORMATION: 2' deoxyribonucleotide

<400> SEQUENCE: 30
gcgugaauag ccguugaaac gccuuuagag aagcacuagc acgc        44

<210> SEQ ID NO 31
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (22)..(22)
<223> OTHER INFORMATION: 2' deoxyribonucleotide

<400> SEQUENCE: 31
gcgugaauag ccguugaaac gccuuuagag aagcacuagc acgc        44

<210> SEQ ID NO 32
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (32)..(32)
<223> OTHER INFORMATION: 2' deoxyribonucleotide

<400> SEQUENCE: 32
gcgugaauag ccguugaaac gccuuuagag aagcacuagc acgc         44

<210> SEQ ID NO 33
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (22)..(22)
<223> OTHER INFORMATION: 2' deoxyribonucleotide

<400> SEQUENCE: 33
gcgugaauag ccguugaaac gccuuuagag aagcacuagc acgc         44

<210> SEQ ID NO 34
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide

<400> SEQUENCE: 34
gcgugaauag ccguugaaac gccuuuagag aagcacuagc acgc         44

<210> SEQ ID NO 35
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (22)..(22)
<223> OTHER INFORMATION: 2' deoxyribonucleotide

<400> SEQUENCE: 35
gcgugaauag ccguugaaac gccuuuagag aagcacuagc acgc                                44

<210> SEQ ID NO 36
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (1)..(1)
<223> OTHER INFORMATION: 2' deoxyribonucleotide
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (32)..(32)
<223> OTHER INFORMATION: 2' deoxyribonucleotide

<400> SEQUENCE: 36
gcgugaauag ccguugaaac gccuuuagag aagcacuagc acgc                                44

<210> SEQ ID NO 37
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (1)..(1)
<223> OTHER INFORMATION: 2' deoxyribonucleotide
<220> FEATURE:
<221> NAME/KEY: misc_feature
<222> LOCATION: (11)..(11)
<223> OTHER INFORMATION: 2' deoxyribonucleotide
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (32)..(32)
<223> OTHER INFORMATION: 2' deoxyribonucleotide

<400> SEQUENCE: 37
gcgugaauag ccguugaaac gccuuuagag aagcacuagc acgc                                44

<210> SEQ ID NO 38
<211> LENGTH: 46
<212> TYPE: DNA
<213> ORGANISM: artificial
<220> FEATURE:
<223> OTHER INFORMATION: synthetic

```
<220> FEATURE:
<221> NAME/KEY: misc_feature
<223> OTHER INFORMATION: D-RNA/L-RNA
<220> FEATURE:
<221> NAME/KEY: misc_feature
<222> LOCATION: (1)..(2)
<223> OTHER INFORMATION: D-RNA

<400> SEQUENCE: 38
gggcgugaau agccguugaa acgccuuuag agaagcacua gcacgc                46

<210> SEQ ID NO 39
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (1)..(1)
<223> OTHER INFORMATION: 2' deoxyribonucleotide
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (32)..(32)
<223> OTHER INFORMATION: 2' deoxyribonucleotide

<400> SEQUENCE: 39
gcgugaauag ccguugaaac gccuuuagag aagcacuagc acgc                  44

<210> SEQ ID NO 40
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA/L-DNA
<220> FEATURE:
<221> NAME/KEY: misc_feature
<222> LOCATION: (1)..(1)
<223> OTHER INFORMATION: 2' deoxyribonucleotide
<220> FEATURE:
<221> NAME/KEY: misc_feature
<222> LOCATION: (19)..(19)
<223> OTHER INFORMATION: 2' deoxyribonucleotide
<220> FEATURE:
<221> NAME/KEY: misc_feature
<222> LOCATION: (21)..(21)
<223> OTHER INFORMATION: 2' deoxyribonucleotide
<220> FEATURE:
<221> NAME/KEY: misc_feature
<222> LOCATION: (32)..(32)
<223> OTHER INFORMATION: 2' deoxyribonucleotide

<400> SEQUENCE: 40
gcgugaauag ccguugaaac gccuuuagag aagcacuagc acgc                  44

<210> SEQ ID NO 41
<211> LENGTH: 36
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 41
wauugccgaw uguaacgccu uwagagaaag cacuag                               36

<210> SEQ ID NO 42
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 42
wauugccgwu guaacgccuu wagagaaagc acuag                                35

<210> SEQ ID NO 43
<211> LENGTH: 34
<212> TYPE: RNA
<213> ORGANISM: Artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 43
aauagccguu gaaacgccuu uagagaagca cuag                                 34

<210> SEQ ID NO 44
<211> LENGTH: 34
<212> TYPE: RNA
<213> ORGANISM: Artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 44
aauagccgau gaaacgccuu uagagaagca cuag                                 34

<210> SEQ ID NO 45
<211> LENGTH: 35
<212> TYPE: RNA
<213> ORGANISM: Artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 45
aauagccgaa ugaaacgccu uaagagaagc acuag                                35
```